(12) United States Patent
Foody et al.

(10) Patent No.: US 7,419,809 B2
(45) Date of Patent: Sep. 2, 2008

(54) METHOD FOR GLUCOSE PRODUCTION WITH A MODIFIED CELLULASE MIXTURE

(75) Inventors: Brian Foody, Ontario (CA); Theresa C. White, Ontario (CA); Jeffrey S. Tolan, Ontario (CA); Jennifer Donaldson, Ontario (CA)

(73) Assignee: Iogen Energy Corporation, Ontario (CA)

( * ) Notice: Subject to any disclaimer, the term of this patent is extended or adjusted under 35 U.S.C. 154(b) by 563 days.

(21) Appl. No.: 10/381,442

(22) PCT Filed: Sep. 25, 2001

(86) PCT No.: PCT/CA01/01355

§ 371 (c)(1),
(2), (4) Date: Sep. 24, 2003

(87) PCT Pub. No.: WO02/24882

PCT Pub. Date: Mar. 28, 2002

(65) Prior Publication Data

US 2004/0053373 A1    Mar. 18, 2004

Related U.S. Application Data

(60) Provisional application No. 60/234,580, filed on Sep. 25, 2000.

(51) Int. Cl.
*C12P 1/00* (2006.01)
*C12P 19/00* (2006.01)
*C12P 19/02* (2006.01)
*C12P 19/14* (2006.01)
*C12N 9/00* (2006.01)

(52) U.S. Cl. .............................. 435/99; 435/41; 435/72; 435/105; 435/183

(58) Field of Classification Search ........................ None
See application file for complete search history.

(56) References Cited

U.S. PATENT DOCUMENTS

| | | | |
|---|---|---|---|
| 3,932,307 A | 1/1976 | Setterquist | |
| 4,237,226 A | 12/1980 | Grethlein | |
| 4,461,648 A | 7/1984 | Foody | |
| 4,826,566 A | 5/1989 | Burkart | |
| 4,894,338 A * | 1/1990 | Knowles et al. | 435/91.41 |
| 5,120,463 A | 6/1992 | Bjork et al. | |
| 5,298,405 A | 3/1994 | Nevalainen et al. | |
| 5,730,837 A | 3/1998 | Black et al. | |
| 5,837,515 A | 11/1998 | Suominen et al. | |
| 5,859,236 A | 1/1999 | Burkart | |
| 5,874,276 A | 2/1999 | Fowler et al. | |
| 5,916,799 A | 6/1999 | Foody et al. | |
| 5,922,579 A | 7/1999 | Fagerstrom et al. | |
| 6,184,019 B1 | 2/2001 | Miettinen-Oinonen et al. | |
| 6,228,629 B1 | 5/2001 | Paloheimo et al. | |

FOREIGN PATENT DOCUMENTS

WO    WO 95/16782 A1    6/1995

OTHER PUBLICATIONS

Suurnakki, A., et al. "*Trichoderma reesei* cellulases and their core domains in the hydrolysis and modification of chemical pulp", Cellulose. Jun. 2000, 7(22), 189-209.*

Kotiranta, P., et al., "Adsorption and Activity of *Trichoderma reesei* Cellobiohydrolase I, Endoglucanase II, and the Corresponding Core Proteins on Stem Pretreated Willow," Appl. Biochem. Biotechnol. 81:81-90, Humana Press Inc. (Aug. 1999).

Nidetzky, B., et al., "Cellulose hydrolysis by the cellulases from *Trichoderma reesei*: adsorptions of two cellobiohydrolases, two endocellulases and their core proteins on filter paper and their relation to hydrolysis," Biochem. J. 303:817-823, Portland Press On Behalf Of The Biochemical Society (1994).

International Search Report for International Patent Application No. PCT/CA01/01355, mailed Jul. 19, 2002.

Barr, B.K., et al., "Identification of Two Functionally Different Classes of Exocellulases," Biochemistry 35:586-592, American Chemical Society (1996).

Beldman, G., et al., "Adsorption and Kinetic Behavior of Purified Endoglucanases and Exoglucanases from *Trichoderma viride*," Biotechnol. Bioeng. 30:251-257, John Wiley & Sons, Inc. (1987).

Birch, P.R.J., "Targeted differential display of abundantly expressed sequences from the basidiomycete *Phanerochaete chrysosporium* which contain regions coding for fungal cellulose-binding domains," Curr. Genet. 33:70-76, Springer-Verlag (1998).

(Continued)

*Primary Examiner*—Sandra Saucier
*Assistant Examiner*—Aaron J Kosar
(74) *Attorney, Agent, or Firm*—Fitzpatrick, Cella, Harper & Scinto

(57) ABSTRACT

The present invention pertains to a method of converting cellulose to glucose by treating a pretreated lignocellulosic substrate with an enzyme mixture comprising cellulase enzyme and a modified CBHO, wherein the modified CBHI is present in the enzyme mixture at an amount relative to all CBHI-type enzymes from about 15% to about 100% (w/w), depending upon the modified CBHI used. The pretreated lignocellulosic substrate is selected from the group consisting of agricultural residues, residues after starch or sugar removal dedicated ethanol crops forestry products, and pulp and paper products, or combinations thereof.

36 Claims, 6 Drawing Sheets

OTHER PUBLICATIONS

Fan, L.T., et al., "Evaluation of Pretreatments for Enzymatic Conversion of Agricultural Residues," *Biotechnol. Bioeng. Symp. No.* 11:29-45, John Wiley & Sons, Inc. (1981).

Foody, P., et al., "Final Report. Optimization of Steam Explosion Pretreatment," U.S. Department of Energy Report ET230501, U.S. Department of Energy, Section 9, pp. 201-233; Appendix C, pp. 313-329 (1980).

Gilkes, N.R., et al., "The Adsorption of a Bacterial Cellulase and Its Two Isolated Domains to Crystalline Cellulose," *J. Biol. Chem.* 267:6743-6749, The American Society for Biochemistry and Molecular Biology (1992).

Grethlein, H.E., and Converse, A.O., "Common Aspects of Acid Prehydrolysis and Steam Explosion for Pretreating Wood," *Biores. Tech.* 36:77-82, Elsevier Science Publishers Ltd. (1991).

Grohmann, K., et al., "Optimization of Dilute Acid Pretreatment of Biomass," *Biotechnol. Bioeng. Symp. No.* 15:59-80, John Wiley & Sons Inc. (1985).

Henrissat, B., "Enzymology of Cell-Wall Degradation," *Biochem. Soc. Trans.* 26:153-156, Portland Press Ltd. (1998).

Henrissat, B., and Bairoch, A., "Updating the sequence-based classification of glycosyl hydrolases," *Biochem. J.* 316:695-696, Portland Press Ltd. (1996).

Kim, D.W., et al., "Adsorption behaviors of two cellobiohydrolases and their core proteins from *Trichoderma reesei* on Avicel PH 101," *Biotechnol. Lett.* 19:893-897, Chapman & Hall (1997).

Knappert, D., et al., "Partial Acid Hydrolysis of Cellulosic Materials as a Pretreatment for Enzymatic Hydrolysis," *Biotechnol. Bioeng.* 22:1449-1463, John Wiley & Sons, Inc. (1980).

Kyriacou, A., et al., "Reversibility and Competition in the Adsorption of *Trichoderma reesei* Cellulase Components," *Biotechnol. Bioeng.* 33:631-637, John Wiley & Sons, Inc. (1989).

Limam, F., et al., "Two cellobiohydrolases of *Penicillium occitanis* mutant Pol 6: Purification and properties," *Enzyme Microb. Technol.* 17:340-346, Elsevier Science Inc. (1995).

Linder, M., et al., "Identification of functionally important amino acids in the cellulose-binding domain of *Trichoderma reesei* cellobiohydrolase I," *Prot. Sci.* 4:1056-1064, Cambridge University Press (1995).

Linder, M., et al., "Design of a pH-dependent cellulose-binding domain," *FEBS Lett.* 447:13-16, Elsevier Science B.V. (Mar. 1999).

Parsiegla, G., et al., "Crystal Structures of the Cellulase Cel48F in Complex with Inhibitors and Substrates Give Insights into Its Processive Action," *Biochemistry* 39:11238-11246, American Chemical Society (Aug. 2000).

Penttilä, M., et al., "Homology between cellulase genes of *Trichoderma reesei*: complete nucleotide sequence of the endoglucanase I gene," *Gene* 45:253-263, Elsevier Science Publishers B.V. (1986).

Saloheimo, M., et al., "EGIII, a new endoglucanase from *Trichoderma reesei*: the characterization of both gene and enzyme," *Gene* 63:11-21, Elsevier Science Publishers B.V. (1988).

Saloheimo, A., et al., "Small endoglucanase from *Trichoderma reesei*, cloned by expression in yeast," in *Trichoderma reesei Cellulases and Other Hydrolases. Enzyme structures, Biochemistry, Genetics and Applications*, vol. 8, Suominen, P., and Reinikainen, T., eds., Foundation for Biotechnical and Industrial Fermentation Research, Helsinki, Finland, pp. 139-146 (1993).

Schülein, M., "Cellulases of *Trichoderma reesei*," *Meth. Enzymol.* 160:234-242, Academic Press, Inc. (1988).

Schülein, M., "Enzymatic properties of cellulases from *Humicola insolens*," *J. Biotechnol.* 57:71-81, Elsevier Science B.V. (1997).

Shen, H., et al., "Cellobiohydrolase B, a second exo-cellobiohydrolase from the cellulolytic bacterium *Cellulomonas fimi*," *Biochem. J.* 311:67-74, Portland Press Ltd. (1995).

Shoemaker, S., et al., "Molecular Cloning of Exo-Cellobiohydrolase I Derived from *Trichoderma reesei* Strain L27," *BioTechnology* 1:691-696, Nature Publishing Co. (1983).

Teeri, T., et al., "The Molecular Cloning of the Major Cellulase Gene From *Trichoderma reesei*," *Biotechnology* 1:696-699, Nature Publishing Co. (1983).

Teeri, T.T., et al., "Homologous domains in *Trichoderma reesei* cellulolytic enzymes: gene sequence and expression of cellobiohydrolase II," *Gene* 51:43-52, Elsevier Science Publishers B.V. (1987).

Teeri, T.T., et al., "Domain function in *Trichoderma reesei* cellobiohydrolases," *J. Biotechnol.* 24:169-176, Elsevier Science Publishers B.V. (1992).

Teeri, T.T., and Koivula, A., "Cellulose degradation by native and engineered fungal cellulases," *Carbohydr. Eur.* 12:28-33, Carbohydrate Research Foundation (1995).

Teeri, T.T., et al., "*Trichoderma reesei* cellobiohydrolases: why so efficient on crystalline cellulose?" *Biochem. Soc. Trans.* 26:173-178, The Biochemical Society (1998).

Tomme, P., et al., "Studies of the cellulolytic system of *Trichoderma reesei* QM 9414. Analysis of domain function in two cellobiohydrolases by limited proteolysis," *Eur. J. Biochem.* 170:575-581, Springer International (1988).

Van Tilbeurgh, H., et al., "Limited proteolysis of the cellobiohydrolase I from *Trichoderma reesei*," *FEBS Lett.* 204:223-227, Elsevier Science Publishers B.V. (1986).

Duarte, et al., "*Aspergilli* and Lignocellulosics: Enzymology and biotechnological applications"; FEMS Microbiology Reviews 13 (1994) 377-86.

Ooshima, et al., "Enhancement of Enzymatic Hydrolysis of Cellulose by Surfactant"; Biotechnology and Bioengineering, vol. XXVIII (1986) 1727-34.

Kaar, et al., "Benefits from Tween During Enzymic Hydrolysis of Corn Stover"; Department of Chemical Engineering, Texas A&M University; Biotechnology and Bioengineering, vol. 59, No. 4 (1998) 419-27.

Eriksson, et al., "Mechanism of Surfactant Effect in Enzymatic Hydrolysis of Lignocellulose"; Enzyme and Microbial Technology vol. 31 (2002) 353-64.

Karlsson, et al., "Hydrolysis of Steam-Pretreated Lignocellulose"; Applied Biochemistry and Biotechnology; vol. 82, No. 3 (1999) 243-58.

Henrissat, et al., "Synergism of Cellulases from *Trichoderma reesei* in the Degradation of Cellulose"; Biotechnology, vol. 3 (1985) 722-26.

Schulein, "Enzymatic Properties of Cellulases from *Humicola insolens*"; Journal of Biotechnology vol. 57 (1997) 71-81.

Srisodsuk, "Mode of Action of *Trichoderma reesei* Cellbiohydrolase I on Crystalline Cellulose"; VTT Biotechnology and Food Research (1994) 3-109.

Kotiranta, et al., "Adsorption and Activity of *Trichoderma reesei* Cellobiohydrolase I, Endoglucanase II, and the Corresponding Core Proteins on Steam Pretreated Willow"; Applied Biochemistry and Biotechnology, vol. 81, No. 2 (1999) 81-90.

Van Tilbeurgh, et al., "Limited Proteolysis of the Cellobiohydrolase I from *Trichoderma ressei*"; FEBS Letters, vol. 204, No. 2 (1986) 223-27.

Chen, et al., "Three Forms of Cellobiohyrdolase I from *Trichoderma reesei*"; Biochemistry and Molecular Biology International, vol. 30, No. 5 (1993) 901-10.

Tomme, et al., "Studies of the Cellulolytic System of *Trichoderma reesei* QM 9414"; Eur. J. Biochem., vol. 170 (1988) 575-81.

Suurnakki, et al., "*Trichoderma reesei* Cellulases and their Core Domains in the Hydriolysis and Modification of Chemical Pulp"; Cellulose, vol. 7 (2000) 189-209.

Nidetzky, et al., "Cellulose Hydrolysis by the Cellulases from *Trichoderma reesei*: A New Mode for Synergistic Interaction"; Biochem. J., vol. 298 (1994) 705-10.

Baker, et al., "Hydrolysis of Cellulose Using Ternary Mixtures of Purified Cellulases"; Applied Biochemistry and Biotechnology, vol. 70-72, (1998) 395-403.

Van Tilbeurgh, et al., "Separation of Endo- and Exo-type Cellulases using a New Affinity Chromatography Method"; vol. 169, No. 2 (1984) 215-18.

Pakula, et al., "Monitoring the Kinetics of Glycoprotein Synthesis and Secretion in the Filamentous Fungus *Trichoderma reesei*: Cellobiohydrolase I (CBHI) as a Model Protein"; Microbiology, vol. 146 (2000) 223-32.

Vinzant, et al., "Fingerprinting *Trichoderma reesei* Hydrolases in a Commercial Cellulase Preparation"; Applied Biochemistry and Biotechnology, vol. 91 (2001) 99-107.

Moeti, et al., "Characterization of Phase and Emulsion Behavior . . . ", Clark Atlanta University (2001) 4-5.

Dence, et al., Pulp Bleaching Principles and Practice (1996) 9-12.

\* cited by examiner

METHOD FOR GLUCOSE PRODUCTION WITH A MODIFIED CELLULASE MIXTURE

CROSS REFERENCE TO RELATED APPLICATIONS

This application is the National Phase of International Application No. PCT/CA01/01355, filed Sep. 25, 2001, which claims the benefit of U.S. Provisional Application No. 60/234,580, filed Sep. 25, 2000.

The present invention relates to the enzymatic conversion of celluose to glucose. More specifically, the present invention provides a method for the conversion of pretreated lignocellulosic substrates using modified CBHI protein, and the recovery and reuse of the modified CBHI protein.

BACKGROUND OF THE INVENTION

A complete list of references can be found at the end of the specification.

Cellulose is one of the most abundant polymers found in nature and consists of glucose units connected by beta 1,4 linkages. The beta 1,4 linkages which connect individual glucose units are not easily degraded or depolymerized. However, there exists a variety of cellulase enzymes which are capable of enzymatically hydrolyzing cellulose.

Cellulases are enzymes produced by a number of microorganisms which catalyse the hydrolysis of cellulose to products such as glucose, cellobiose, and other cellooligosaccharides. Cellulase is usually a generic term denoting a multienzyme mixture comprising exo-cellobiohydrolases (CBH), endoglucanases (EG) and β-glucosidases. Cellulase produced by the filamentous fingi *Trichoderma longibrachiatum* comprises at least two cellobiohydrolase enzymes termed CBHI and CBBE and at least 4 EG enzymes.

Cellulase enzymes work synergistically to degrade cellulose to glucose. CBHI and CBHII generally act on the ends of the glucose polymers in cellulose microfibrils liberating cellobiose (Teeri and Koivula, 1995) while the endoglucanases act at random locations on the cellulose. Together these enzymes hydrolyse cellulose to smaller cello-oligosaccharides such as cellobiose. Cellobiose is hydrolysed to glucose by β-glucosidase.

The genes encoding CBHI, CBH II (Shoemaker et al., 1983; Teeri et al., 1987), EG I and EG II (Penttila et al., 1986; Saloheimo et al., 1988) have been cloned and isolated from filamentous fungi such as *T. reesei* and *T. longibrachiatum*. CBHI, CBH II and most of the major EG enzymes comprise a catalytic core domain and a cellulose binding domain (CBD) separated by a flexible linker region. The cellulose binding domain (CBD) promotes adsorption of the enzyme to regions of the cellulosic substrate (Tomme et al., 1988; Gilkes et al, 1992), while the core domain is responsible for catalysing the cleavage of cellulose. The linker region may ensure an optimal interdomain distance between the core domain and the cellulose binding domain (Teeri et al., 1992).

Proteins consisting of either the isolated CBD or the core protein have been produced and studied. Core proteins of CBHI are also found in amounts of less than about 10 % in cellulase mixtures obtained from natural sources. Studies on the isolated fungal catalytic domain (core protein) suggest that this protein is capable of binding to cellulose although with reduced affinity compared to the native Polo) protein (Tomme et al., 1988). The strong binding imparted to cellulases by its CBD suggests that the adsorption of several cellulases to cellulose is essentially irreversible (Beldman et al., 1987; Kyriacou et al., 1989)

CBHI core protein from *Trichoderma reesei* does not bind as tightly to cellulose as CBHI. The CBHI core protein is fully active against small soluble substrates such as the chromophoric glycosides derived from the cellodextrins and lactose. However, its activity against an insoluble cellulosic substrates such as Avicel (a crystalline type of cellulose) is greatly reduced compared to CBHI (Van Tilbeurgh et al., 1986). Van Tilbeurgh showed that CBHI-core was less than 1% as active as CBHI. This was attributed to the fact that 88% of the CBHI adsorbed to the cellulose versus only 36% of the CBHI-core protein. Kim et al., (1997) examined the absorption and activities of CBHI, CBHI core and other protein mixtures on Avicel. They disclose that CBMI core produced less than ¼ the amount of reducing sugar from Avicel than CBHI. The higher rate of hydrolysis by CBHI was attributed to its better binding. In similar experiments with steam-pretreated willow, Kotiranta et al. (1999) observed a drastically reduced hydrolysis rate for CBHI core compared to intact CBHI and concluded that CBHI needs a CBD for efficient adsorption and hydrolysis. Nidetsky et al. (1994) observed similar trends between CBHI-core and CBHI. Over 80% of the CBHI adsorbed to cellulose filter paper, compared with only 40% of CBHI-core. The rate of hydrolysis of the core and CBHI were directly proportional to the amount of adsorbed protein, with CBHI being more than twice as active as CBHI-core. These studies indicate that there is no advantage in using CBHI-core rather than CBHI for cellulose hydrolysis, since the activity of CBHI-core against crystalline cellulose is much slower than CBHI.

The conversion of cellulose from cellulosic material into glucose is important in many industrial processes, such as the bioconversion of cellulose to fuel ethanol. Unfortunately, cellulose contained in most plant matter is not readily convertible to glucose, and this step represents a major hurdle in the commercialization of such a process. The efficient conversion of cellulose from cellulosic material into glucose was originally thought to involve liberating cellulose and hemicellulose from their complex with lignin. However, more recent processes focus on increasing the accessibility to cellulose within the lignocellulosic biomass followed by depolymerization of cellulose carbohydrate polymers to glucose. Increasing the accessibility to cellulose is most often accomplished by pretreating the cellulosic substrate.

The goal of most pretreatment methods is to deliver a sufficient combination of mechanical and chemical action, so as to disrupt the fiber structure and improve the accessibility of the feedstock to cellulase enzymes. Mechanical action typically includes the use of pressure, grinding, milling, agitation, shredding, compression/expansion, or other types of mechanical action. Chemical action typically includes the use of heat (often steam), acid, and solvents. For example, one of the leading approaches to pretreatment is by steam explosion, using the process conditions described in (U.S. Pat. No. 4,461,648) and also in Foody et al., 1980), both of which are incorporated herein by reference). In this process, lignocellulosic biomass is loaded into a steam gun and up to 5% acid is optionally added to the biomass in the steam gun or in a presoak prior to loading the steam gun. The steam gun is then filled very quickly with steam and held at high pressure for a set length of cooking time. Once the cooking time elapses, the vessel is depressurized rapidly to expel the pretreated biomass.

Another approach described in U.S. Pat. No. 4,237,226, discloses the pretreatment of oak, newsprint, poplar, and corn stover by a continuous plug-flow reactor, a device that is similar to an extruder. Rotating screws convey a feedstock slurry through a small orifice, where mechanical and chemical action break down the fibers.

Pretreatment has been suggested to enhance delignification of the cellulosic substrate (Fan et al., 1981), create micropores by the removal of the hemicellulose, change the crystallinity of the substrate, and reduce the degree of polymerization of the cellulose (Knappert et al., 1980) and increase the surface area of the cellulosic substrate (Grethlein and Converse, 1991; Grohman et al., 1985).

Unfortunately, to date the approach of a pretreatment coupled with enzyme hydrolysis has not been able to produce glucose at a sufficiently low cost, so as to make the conversion of cellulose to ethanol commercially attractive. Even with the most efficient of the currently known pretreatment processes, the amount of cellulase enzyme required to convert cellulose to glucose is high and this represents a significant cost in ethanol production. The option of adding less cellulase to the system usually decreases the amount of glucose produced to an unacceptable extent. The approach of decreasing the amount of enzyme required by increasing the length of time that the enzyme acts on the cellulose leads to uneconomical process productivity, stemming from the high cost associated with retaining the enzymatic mixtures in hydrolysis tanks.

Thus there is a need within the art to identify new methods which enhance the conversion of cellulose within a cellulosic substrate to glucose. Further there is a need in the art to identify enzymes or mixtures of enzymes which enhance the conversion of cellulose to glucose and which are recoverable, recyclable, and reusable.

It is an object of the present invention to overcome drawbacks of the prior art.

The above object is met by a combination of the features of the main claims. The sub claims disclose further advantageous embodiments of the invention.

SUMMARY OF THE INVENTION

The present invention relates to the enzymatic conversion of cellulose to glucose.

According to the present invention, there is provided a method of converting cellulose to glucose comprising; treating a pretreated lignocellulosic cellulosic substrate with an enzyme mixture comprising cellulase enzyme and a modified CBHI, wherein the modified CBHI is present in said enzyme mixture at an amount relative to all CBHI-type enzyme of from about 55 to about 100%. Preferably, the amount of modified CBHI in the enzyme mixture is from about 70 to about 100%. More preferably, the amount of modified CBHI in the enzyme mixture is from about 80 to about 100%. Furthermore, this invention pertains to the above method wherein the modified CBHI is recovered following the step of treating. This invention also pertains to the above method wherein the modified CBHI is selected from CBHI core, CBHI core plus linker and CBHI with inactivated cellulose binding domain. Also, the present invention relates to the above method wherein the pretreated lignocellulosic substrate is pretreated using an acid steam cook.

This invention also pertains to a method of converting cellulose within a cellulosic substrate into glucose comprising; treating a pretreated lignocellulosic substrate with an enzyme mixture comprising CBHI, CBI-HI, EG I, EG II, β glucosidase and modified CBHI, wherein the modified CBHI is present in said enzyme mixture at an amount relative to all CBHI-type enzyme of from about 55 to about 100%. Preferably, the amount of modified CBHI in the enzyme mixture is from about 70 to about 100%. More preferably, the amount of modified CBHI in the enzyme mixture is from about 80 to about 100%. Furthermore, this invention pertains to the above method wherein the modified CBHI is recovered following the step of treating. This invention also pertains to the method as just described wherein the modified CBHI is selected from CBHJ core, CBHI core plus linker and CBHI with inactivated cellulose binding domain.

The present invention embraces methods as defined above wherein the pretreated lignocellulosic substrate is selected from the group consisting of agricultural residues, residues after starch or sugar removal, dedicated ethanol crops, forestry products, and pulp and paper products or combinations thereof Preferably, the agricultural residues are selected from the group consisting of corn stover, wheat straw, barley straw; soybean stover; the residues after starch or sugar removal are selected from the group consisting of oat hulls, rice hulls, sugar cane bagasse, and corn fibre; the dedicated ethanol crops are selected from the group consisting of switch grass, miscanthus, cord grass, and rye grass; the forestry products are selected from the group consisting of hardwood, softwood, Eucalyptus, and sawdust; and the pulp and paper products is solka floc.

The present invention also relates to the methods of lignocellulosic hydrolysis as defined above, wherein the lignocellulosic substrate is characterized as having an $E_I$ of at least about 0.5, and an $R_I$ from about 45 to about 100. This invention also includes the above methods wherein the $E_I$ is from about 1.0 to about 4.0, and the $R_I$ is from about 60 to about 100.

Also included within the present invention, is a method as defined above wherein the pretreated lignocellulosic substrate is present in the enzyme mixture at a concentration of about 1 wt % to about 25 wt % in aqueous slurry. Preferably, the lignocellulosic substrate is present in the enzyme mixture at a concentration of about 10 wt % to about 16 wt % in aqueous slurry.

The present invention also pertains to a method for hydrolyzing cellulose to glucose comprising treating a pretreated lignocellulosic substrate characterized with an $E_I$ of from about 0.5 to about 4, with an enzyme mixture comprising cellulase enzyme with CBHI-type enzymes, wherein said CBHI-type enzymes comprise 20% to 100% CBHI-core.

This invention also provides a method of converting cellulose within a cellulosic substrate into glucose comprising; treating a pretreated lignocellulosic substrate with an enzyme mixture comprising CBHI core and one or more of CBHI, CBHII, EG I, EG II, and β-glucosidase, wherein the CBHI core is present in the enzyme mixture at an amount relative to all CBHI-type enzyme of from about 15 to about 100%. Preferably the amount of CBHI core in the enzyme mixture is from about 50 to about 100%. More preferably the amount of CBHI core in the enzyme mixture is from about 80 to about 100%.

Furthermore, the present invention embraces a method for converting cellulose to glucose comprising treating a pretreated lignocellulosic substrate with an enzyme mixture comprising CBHI-core plus linker, and one or more of CBHI, CBHII, EG I, EG II, and β-glucosidase wherein said CBHI-core plus linker is present in said enzyme mixture in an amount of about 50% to about 100%, relative to all CBHI-type enzymes. Preferably the amount of CBHI-core plus linker in the enzyme mixture is from about 70% to about 100%. More preferably, the amount of CBHI-core plus linker in said enzyme mixture is from about 80% to about 100%.

The present invention also provides a cellulase composition comprising modified CBHI and one or more of CBHI, CBHII, EG I, EG II, and β-glucosidase, wherein the modified CBHI is present in the cellulase composition at an amount relative to all CBHI-type enzyme of from about 55 to about 100 wt %. Preferably the modified CBHI is from about 70 to about 100 wt %, and more preferably from about 80 to about 100 wt %. The invention also includes the cellulase composition as just defined wherein the modified CBHI is a modified Trichoderma CBHI.

This invention embraces a cellulase composition comprising a CBIH type enzyme and one or more of CBHII, EG I, EG II, and β-glucosidase, wherein CBHI core is present in the cellulasae composition at an amount relative to all CBHI-type enzyme of from about 15 to about 100 wt %. Preferably the CBHI core is from about 50 to about 100 wt %, and more preferably from about 80 to about 100 wt %. This invention also relates the the cellulase composition as just defined wherein the CBHI core is obtained from Trichoderma CBHI.

Also included in the present invention is a cellulase composition comprising modified CBHI and one or more of CBHII, EG I, EG II, and β-glucosidase, wherein the modified CBHI is present in the cellulase composition from about 50 to about 90 wt % relative to other cellulase enzymes. Preferably the modified CBHI is a modified Trichoderma CBHI.

This summary does not necessarily describe all necessary features of the invention but that the invention may also reside in a sub-combination of the described features.

BRIEF DESCRIPTION OF THE DRAWINGS

These and other features of the invention will become more apparent from the following description in which reference is made to the appended drawings wherein:

FIG. 1 shows a graphical representation of the percentage conversion of cellulose to glucose using different pretreated lignocellulosic substrates and varying amounts of CBHI and CBHI core protein.

FIG. 2 shows a graphical representation of the effect of varying the concentration of cellulosic substrate within a reaction mixture.

DESCRIPTION OF PREFERRED EMBODIMENT

Figure 1A:
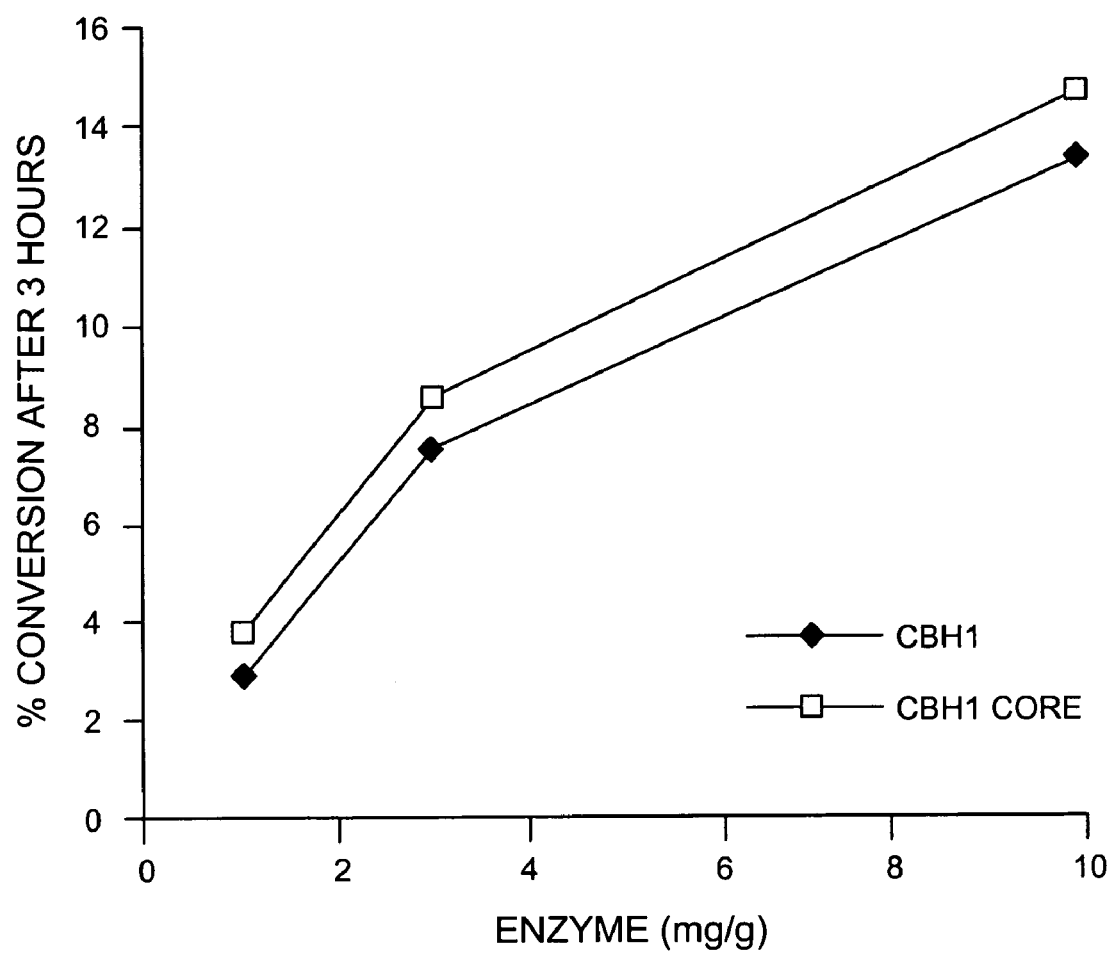
FIG. 1A shows hydrolysis of pretreated washed corn stover using increasing amounts of either CBHI or CBHI core.

The present invention relates to the enzymatic conversion of cellulose to glucose. More specifically, the present invention provides a method for the conversion of pretreated lignocellulosic substrates using modified CBHI protein, and the recovery and reuse of the modified CBHI protein.

The following description is of a preferred embodiment by way of example only and without limitation to the combination of features necessary for carrying the invention into effect.

It is well known in the art that cellulose in many lignocellulosic materials may not be readily hydrolysable by enzymes. Thus, it is preferred that the cellulosic substrate for enzymatic hydrolysis as described herein be pretreated prior to being treated with enzymes.

There are a number of pretreatment processes known in the art that employ thermal, mechanical, chemical, or combinations of these methods to disrupt the fiber structure of cellulosic substrates and which enhance subsequent enzymatic hydrolysis of the cellulosic substrate. Any pretreatment process which enhances the enzymatic hydrolysis may be employed in combination with the method of the present invention. For example, but not wishing to be limiting, the pretreatment process disclosed in U.S. Pat. No. 4,461,648 or U.S. Pat. No. 4,237,226 (both of which are incorporated herein by reference) may be used, or any of the pulping processes known within the art (e.g. Rydholm S. A. 1985, Pulping Processes, Kreiger Pub. Co, which is incorporated herein by reference), including kraft, sulfite, mechanical, thermal, and chemi-thermal-mechanical pulping. Alternatively, pretreatment processes may also involve the addition of organic solvents to aid in the fractionation of lignin, cellulose and hemicellulose from lignocellulosic raw materials. These pretreatment processes may include but are not limited to those disclosed in U.S. Pat. No. 3,932,307 which teaches impregnating raw lignocellulosic material with a solution of lignin-solubilizing reactant in an organic solvent and subsequently immersing the impregnated material in a solvent that is neither soluble nor miscible with the reactant-containing solution with which the lignocellulosic material has been impregnated; U.S. Pat. No. 4,826,566, which uses solvent mixtures such as triethylene glycol with arylsulfonic or other acids; U.S. Pat. No. 5,859,236 which teaches impregnating lignocellulosic material with an extraction liquor containing a glycol and Lewis acid; and U.S. Pat. No. 5,730,837 which teaches treating lignocellulosic material with a combination of alcohol, water and water immiscible organic solvent, for example, a ketone.

A preferred pretreatment process is an acid-steam cook, as disclosed in U.S. Pat. No. 4,461,648, wherein an acid, for example sulfuric acid from about 0 to about 5%, is added to a lignocellulosic substrate, and the acidified mixture is cooked for about 5 seconds to about 2 minutes, at a temperature of about 180 to about 250° C.

Without wishing to be bound by theory, it is thought that the pretreatment process enhances subsequent enzymatic hydrolysis of cellulose by increasing delignification, creating micropores in the cellulose, changing the crystalline form of the cellulose, reducing the polymerization of cellulose, increasing the surface area of cellulose, or combinations thereof. As a large portion of the cellulose within many types of cellulosic substrate is normally unaccessible for enzymatic conversion to glucose without pretreatment, the efficiency of the pretreatment phase can influence the efficiency and commercial application of enzymatically converting cellulose to glucose.

By the term 'cellulosic substrate', it is meant any material comprising cellulose which maybe converted to glucose by enzymatic hydrolysis. The cellulosic substrate is preferably a pretreated lignocellulosic substrate, comprising at least about 10% lignin. For example, but not wishing to be limiting, the cellulosic substrate suitable for pretreatment may comprise:

agricultural residues (lignin content about 15%) such as, but not limited to corn stover, wheat straw, barley straw, soybean stover;

residues following starch or sugar removal, for example but not limited to, oat hulls, rice hulls, corn fibre, sugar cane bagasse, sugar cane pulp;

dedicated ethanol crops, such as, but not limited to switch grass, miscanthus, cord grass, rye grass;

forestry products, for example, but not limited to hardwood (e.g. poplar; lignin content about 25%), softwood (lignin content about 35%), Eucalyptus, and forestry residues, sawdust; and other pretreated lignocellulosic substrates including pulp and paper products, for example but not limited to solka floc, or combinations thereof. Pretreated hardwood, or agricultural residues, including corn stover, oat hulls barley straw or wheat straw cellulosic substrates produced by the method disclosed in U.S. Pat. No. 4,461,648 (which is incorporated herein by reference) are preferred lignocellulosic substrates.

Enzymatic hydrolysis of cellulose may follow pretreatment directly, or alternatively, a number of steps may follow pretreatment and precede enzymatic hydrolysis of cellulose. For example, but not wishing to be limiting, pretreated cellulosic substrate maybe washed with water to remove chemicals, contaminants, or combinations thereof which could hinder the enzymatic conversion of cellulose to glucose.

By "CBHI" it is meant a protein comprising a cellulose binding domain, linker region and a CBHI core region, or derivatives thereof, which digests a cellulose polymer from the reducing end and releases cellobiose. A non limiting example of a derivative of CBHI is phosphorylated CBHI. To date CBHI enzymes have been classified in Family 7 and Family 48 and comprise a range of molecular weights. Preferably, the CBHI is obtained from Trichoderma. The *Trichodernia reesei* CBHI protein is of approximately 65 kDa comprising a C-terminal cellulose binding domain, linker region and a CBHI core region and digests cellulose from the reducing end releasing cellobiose (Shoemaker 1983). However, it is to be understood that CBHI protein may be obtained from other sources as well (Barr et al. 1996, Biochemistry 35:586-592; Birch 1998, Current Genetics 33:70-76; Henrissat 1998, Biochemical society transactions21(2): 153-156; Henrissat and Bairoch 1996, Biochem. J. 316:695-696; Liman et al.1995, Enzyme and Microbial Technology 17:340-346; Parsiegla et al. 2000, Biochemistry 39:11238-11246; Schulein 1997, Journal of Biotechnology 57:71-81; Shen et al., 1995, Biochem. J 311:67-74; Teeri et al.1997, Biochemical society transactions 26(2):173-178; all of which are incorporated herein by reference).

By "CBHI core" it is meant the portion of CBHI comprising the catalytic domain of CBHI, and that is capable of hydrolyzing a cellulosic substrate as defined herein. For example which is not to be considered limiting in any manner Trichoderma CBHI core is approximately 56 kDa. CBHI core may be produced by proteolytic cleavage of the CBHI protein using a suitable protease, for example but not limited to papain (for example, using the method of van Tillbeurgh et al. 1986; Offord et al 1991; both of which are incorporated herein by reference). In this manner, a protease, for example but not limited to papain, may also be added to a crude enzyme mixture to produce CBHI core within the mixture. In this embodiment, depending on the protease, for example but not limited to papain, may also be added to a crude enzyme mixture to produce CBHI core within the mixture. In this embodiment, depending on the protease added, other core enzymes may also be produced. CBHI core may also be produced using recombinant technology, for example, using the method disclosed in U.S. Pat. No. 5,874,276. In this manner CBHI and CBHI core may be co-expressed in the same host organism, or the host may be genetically modified so that native CBHI expression is reduced or eliminated, and supplemented or replaced, respectively, with recombinant CBHI core expression. It is to be understood that CBHI core also includes fragments or derivatives of CBHI core, including substitutions, deletions, insertions within the CBHI core sequence as would be known to one of sill in the art, providing that these fragments and derivatives exhibit CBHI core activity in that they are capable of hydrolysing cellulose. A non limiting example of a derivative CBH core is a phosphorylated CBHI core. It is also to be understood that CBHI core may be isolated form an organism wherein the CBHI protein does not comprise a cellulose binding domain or linker region.

By the term "CBHI core plus linker" it is meant a fragment of a CBHI protein comprising CBHI core protein and the linker amino acid sequence, or a fragment thereof, that joins the CBHI core protein to the CBD of the CBHI protein. The linker portion of the CBHI core plus linker may comprise any length of the amino acid sequence. Further, it is to be understood that CBHI core plus linker also includes fragments or derivatives of CBHI core plus linker, including substitutions, deletions, insertions within the CBHI core plus linker sequence as would be known to one of skill in the art, providing that these fragments and derivatives of CBHI core plus linker exhibit CBHI core activity. A non limiting example of a derivative CBH core plus linker is a phosphorylated CBHI core plus linker. It is also to be understood that CBHI core plus linker may be isolated from an organism wherein the CBHI protein does not comprise a cellulose binding domain.

By the term "CBHI with inactive cellulose binding domain" it is meant a protein comprising CBHI core, or CBHI core plus linker, and a cellulose binding domain (CBD) that has been inactivacted. Inactivation of a CBD may be performed by methods known in the art, for example but not limited to Linder et al. (Linder et al., 1995, Protein Science,4; 1056-1064; and Linder et al., 1999,FEBS Letters 447, 13-16 which are herein incorporated by reference). An inactivated CBD results in a reduced capacity of the CBD to bind cellulose when compared with the binding activity associated with a corresponding wild type CBHI and assayed under identical conditions (for example, as described in binding studies by Linder et al., 1999, FEBS Letters 447, 13-16). Further, it is to be understood that CBHI with inactive cellulose binding domain also includes fragments or derivatives of CBHI including substitutions, deletions, insertions within the CBHI, linker, CBD, or a combination thereof, sequence as would be known to one of skill in the art, providing that these fragments and derivatives exhibit CBHI core activity, and exhibit a reduced capacity to bind cellulose. A non-limiting example of a derivative CBH with inactive cellulose binding domain is a phosphorylated CBIH with inactive cellulose binding domain. It is also to be understood that a CBHI with inactive cellulose binding domain may be isolated from an organism wherein the CBHI protein comprises a cellulose binding domain, however the CBD exhibits poor cellulose binding activity. A CBHI exhibiting poor cellulose binding activity exhibits less than about 70% of the cellulose binding activity of a CBHI obtained from *Trichoderma reesei* using the same substrate. Preferably the CBHI exhibiting poor cellulose binding activity exhibits less than about 50% of the cellulose binding activity of *Trichoderma reesei* CBHI. A range of CBHI enzymes are known in the art and include but are not limited to those disclosed in Barr et al.(1996, Biochemistry 35:586-592), Birch (1998, Current Genetics 33:70-76), Henrissat (1998, Biochemical society transactions21(2): 153-156), Henrissat and Bairoch (1996, Biochem. J. 316: 695-696), Liman et al.(1 995, Enzyme and Microbial Technology 17:340-346), Parsiegla et al.( 2000, Biochemistry 39:11238-11246), Schulein (1997, Journal of Biotechnology 57:71-81), Shen et al., (1995, Biochem. J 311:67-74), and Teeri et al.(1997, Biochemical society transactions 26(2): 173-178; all of which are incorporated herein by reference).

By "modified CBHI" it is meant a protein comprising either CBHI core, CBHI core plus linker, CBHI with inactive cellulose binding domain, or a combination thereof. A modified CBHI protein is characterized as having CBHI core activity, along with a reduced, or no, cellulose binding activity.

As described in more detail below, it has been observed that on several pretreated lignocellulosic substrates, the rate of hydrolysis using a modified CBHI protein, for example but not limited to CBHI core, is equivalent, or in some cases exceeds the rate of hydrolysis observed using CBHI. This is counter to previous reports where CBHI is disclosed as being much faster than CBHI core on pure cellulose. Without wishing to be bound by theory, it is possible that the equivalent activities between CBHI and CBHI core, or other modified CBHI proteins, on pretreated lignocellulose maybe due to the fact that lignocellulosic substrates that have been pretreated, have a large surface area, and this increases access to the modified CBHI protein, such as the CBHI core protein, to digest the substrate. It will be readily appreciated by one of skill in the art, the results observed with CBHI core may also be obtained using modified CBHI as defined herein, comprising either CBHI core plus linker, CBHI with inactive cellulose binding domain or a combination thereof.

Furthermore, it has also been observed that by increasing the concentration of cellulose substrate, modified CBHI, for example but not limited to CBHI core, converts cellulose more quickly (see FIGS. 2 (A) and (B)). Without wishing to be bound by theory, an increased concentration of substrate may reduce migration times of the modified CBHI protein within the reaction mixture thereby increasing the hydrolysis rate of the substrate.

Figure 3:
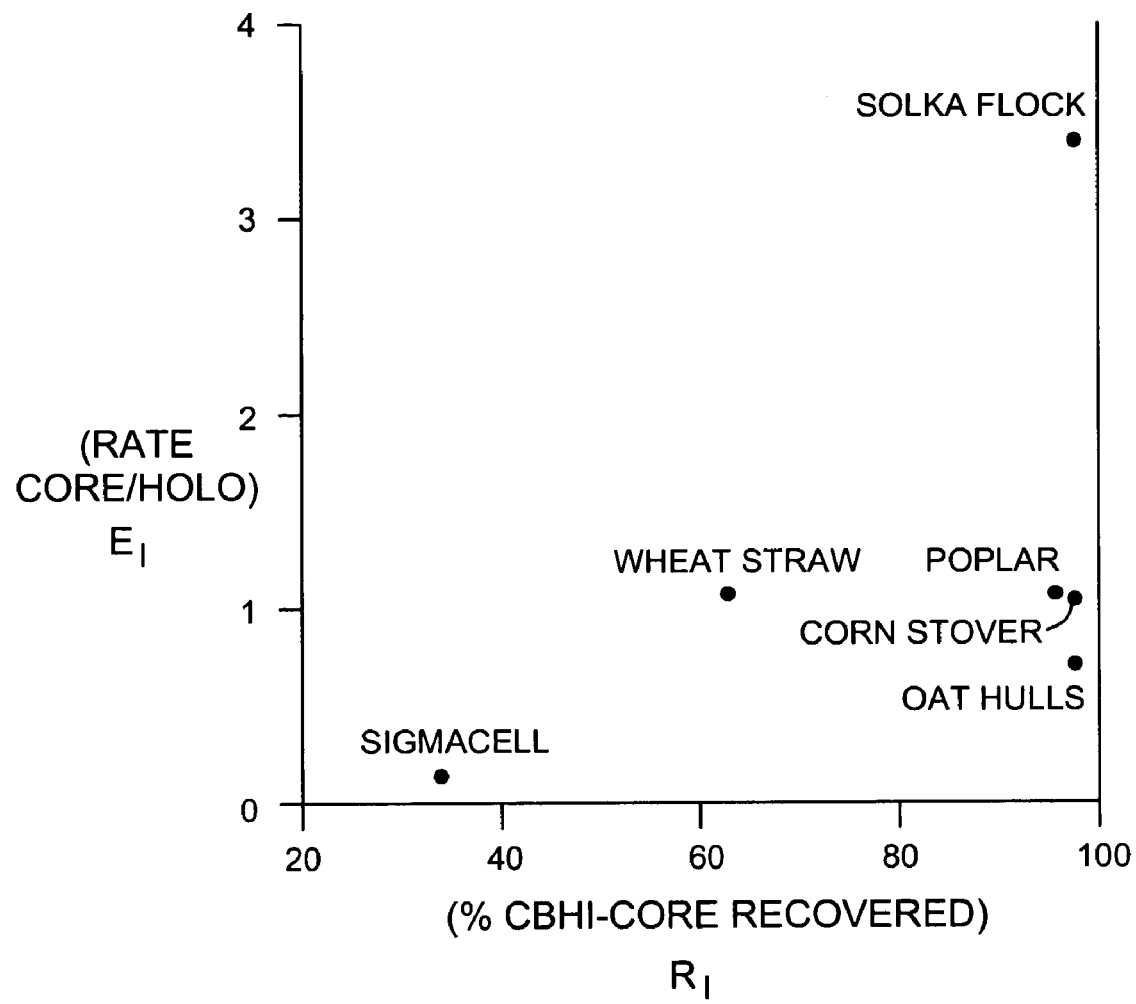
FIG. 3 shows a graphical representation of the relationship between the relative rate of hydrolysis of CBHI core and CBHI, and the amount of CBHI core recovered from the reaction mixture. The high level of recovery of CBHI core is a direct result of the amount of CBHI core in solution in the reaction mixture.

The benefits associated with the use of modified CBHI, for example but not limited to CBHI core, or mixtures of enzymes comprising the CBHI core protein, over that of just CBHI, include the increased ability to recover the modified CBHI from the reaction mixture (especially when compared with CBHI) following digestion (e.g. see Table 3, Example 1, and FIG. 3). Furthermore, with some substrates, there is a higher, or more rapid conversion of the lignocellulosic substrate to glucose using modified CBHI, for example but not limited to CBHI core, when compared with CBHI, thereby reducing costs associated with re-introducing new enzyme into the hydrolysis mixture, and reducing enzyme usage.

Figure 1B:
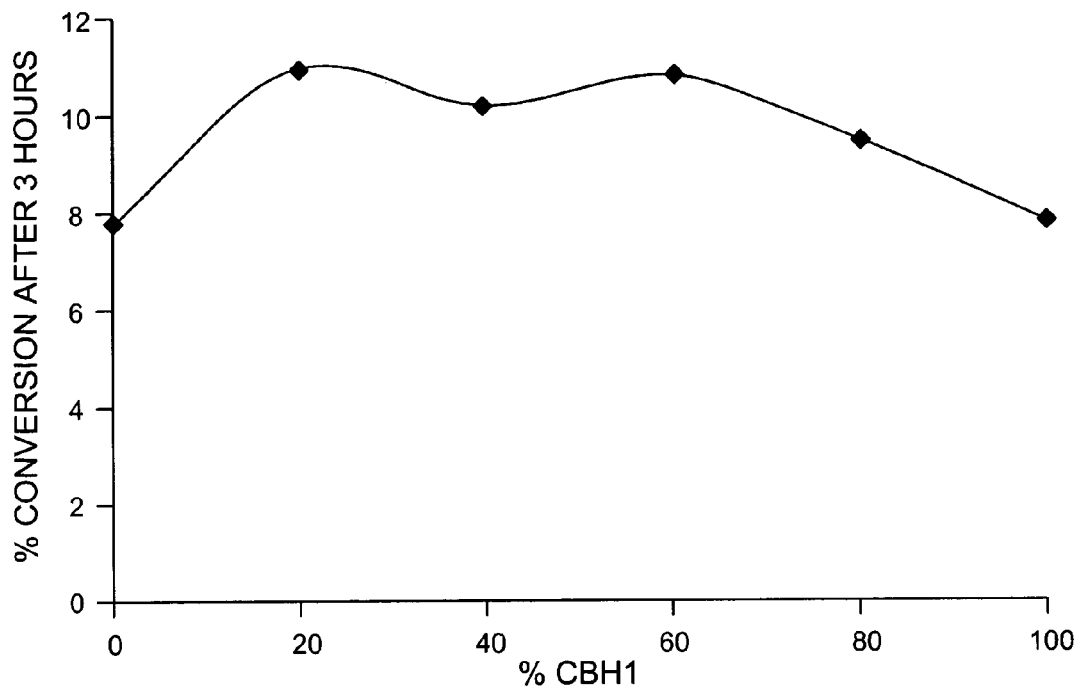
FIG. 1B shows the conversion of pretreated oat hulls after three hours of incubation using various mixtures of CBHI and CBHI core protein.

In some instances, depending upon the cellulosic substrate to be hydrolysed, it may be desirable to use modified CBHI - CBHI mixtures, for example which is not to be considered limiting in any manner CBHI core - CBHI mixtures, to optimize hydrolysis of the substrate (FIGS. 1B and C) . In these circumstances, cost savings may also be achieved due to recovery of the modified CBHI protein and increased reaction rates, since there is only a partial loss of added enzyme, and increased activity permits the use of less enzyme or reduced reaction times.

To practice the invention, the enzymatic hydrolysis of cellulose is carried out using a cellulase enzyme mixture. Those skilled in the art are aware that an efficient cellulase mixture contains CBHI-type, CBHII-type, EG, β-glucosidase, and other enzymes as required to effect the full range of necessary hydrolysis reactions. The skilled practitioner is also aware that the term "CBHI-type" encompasses the holo enzyme. The Trichoderma CBHI has a molecular weight of about 65 Kd comprising the CBHI core, linker, and cellulose binding domain regions. "CBHI-type" also includes:

CBHI-core protein, for example in the case of Trichoderma, having a molecular weight of about 56 Kd,
CBHI-core protein with linker attached ("CBHI core plus linker"), with molecular weight in the case of Trichoderma of about 60 Kd,
phosphorylated CBHI, having for example in Trichodernia, a molecular weight of about 65 Kd,
isolated CBHI CBD (cellulose binding domain), as well as various forms of different degrees of glycosylation and other structural features that occur in small amounts. It is also to be understood that CBHI-type enzyme may also include modified CBHI as described herein, including CBHI with inactivated cellulose binding domain.

In the context of the present invention, the CBHI-type enzymes are preferably at least 20% modified CBHI, for example but not limited to CBHI-core protein. The proportion of modified CBHI protein can account for up to 100% of the total CBHI-type enzyme present.

The determination of the percentage of modified CBHI, for example but not limited to CBHI core, within the CBHI-type enzymes is carried out using a capillary isoelectric focusing (CIEF). The method of CIEF electrophoresis is described in Example 4.

The invention is practiced in a hydrolysis system where the efficiency index $E_I$ is greater than 0.5. The efficiency index, $E_I$, which is measured using the procedures of Example 1, is the ratio of the rate of hydrolysis of modified CBHI, for example but not limited to CBHI-core, to that of intact CBHI where:

$$E_I=[\text{modified CBHI activity}]/[\text{CBHI activity}].$$

The determination of $E_I$ is made at a constant substrate concentration, and is made using a comparable basis of enzyme, for example, on a per mg protein basis. For the determination of $E_I$ as disclosed herein, a substrate concentration of 2% cellulose, and 10 mg of protein was used. The present invention contemplates using lignocellulosic substrates characterized by having an $E_I$ of about 0.5 to about 4.0. A preferred $E_I$ is from about 0.7 to about 2.0. More preferably, the $E_I$ is from about 0.8 to about 1.5.

As described herein, on pretreated lignocellulosic substrates, $E_I$ has a value close to or even exceeding unity. This suggests that modified CBHI, for example but not limited to CBHI-core can hydrolyze these materials as rapidly or more rapidly than CBHI. This finding is in direct opposition to teachings in the literature where the rate of CBHI is much more rapid than CBHI-core (e.g. Kim, 1997; Van Tilbeurgh et al., 1986, Nidetsky et al, 1994).

In an aspect of an embodiment of the present invention, modified CBHI, for example but not limited to CBHI-core protein, is recovered and reused after the hydrolysis. The methods one can use for recovering and reusing soluble proteins are well known in the art and can be applied to any modified CBHI, for example CBHI-core. These methods involve separating the insoluble solids residue from the hydrolysis liquor, and sending the hydrolysis liquor back to fresh (unhydrolyzed) substrate. Alternatively, the enzyme can be removed from the hydrolysis liquor by precipitation, for example, but not limited to pH, salt, temperature precipitation, extraction, for example but not limited to solvent extraction, or filtration, for example, but not limited to ultrafiltration, and added back to the hydrolysis. In the case of enzyme removal using ultrafiltration, a preferred membrane has a MW cut off of about 1,000, to about 20,000. More preferably, the cut off is from about 5,000 to about 10,000.

Therefore, the present invention provides a method of converting cellulose to glucose comprising treating a pretreated lignocellulosic substrate with an enzyme mixture comprising cellulase enzyme and a modified CBH I, wherein the modified CBHI is present in the enzyme mixture at an amount relative to all CBHI-type enzyme of from about 55 to about 100 wt%. Preferably the amount of modified CBHI in said enzyme mixture is from about 70 to about 100wt%. More preferably the amount of modified CBHI in the enzyme mixture is from about 80 to about 100wt%.

The present invention also provides a cellulase composition comprising modified CBHI and one or more of CBHI, CBHII, EG I, EG II, and β-glucosidase, wherein the modified CBHI is present in the cellulase composition at an amount relative to all CBHI-type enzyme of from about 55 to about 100 wt %. Preferably the modified CBHI is from about 70 to about 100wt %, and more preferably from about 80 to about 100 wt %. It is also preferred that the modified CBHI is a modified Trichoderma CBHI.

According to another aspect of the present invention, there is provided a method for converting cellulose to glucose comprising treating a lignocellulosic substrate, with an enzyme mixture comprising CBHI, or a mixture comprising cellulase, and modified CBHI, for example but not limited to CBHI core protein. If a mixture of CBHI and CBHI core is used, the amount of CBHI or CBHI core in the enzyme reaction mixture is from about 10% to about 100% wt % of the CBHI and CBHI core protein (where CBHI +CBHI core comprise up to 100 wt % of the CBHI-type enzymes; see FIGS. 1B and 1C), preferably the amount of CBHI or CBHI core is from about 20% to about 80% wt % of the CBHI and CBHI core protein within the reaction mixture. For example, which is not to be considered limiting in any manner, a suitable reaction mixture may comprise between about 20 wt % CBHI and about 80 wt % CBHI (of the CBHI and CBHI core protein).

According to yet another aspect of the present invention, there is provided a method for converting cellulose to glucose comprising treating a cellulosic substrate with an enzyme mixture comprising CBHI and modified CBHI, for example CBHI core, as the only CBHI-type enzymes and one or more other cellulase enzymes, including CBHII, EG I, EG II, and β-glucosidase, wherein the weight ratio of CBHI or CBHI core, as an example of a modified CBHI, in the enzyme mixture is in the range of from about 10% to about 100% wt % of the CBHI type. Preferably the amount of CBHI or CBHI core is from about 20% to about 80% wt %, of the CBHI type. In this embodiment, the CBHI core may be added to a cellulase mixture (comprising one or more of CBHI, CBHII, EG I, EG II, and β-glucosidase) produced by, for example, but not limited to, a filamentous fungi. Preferably, the filamentous fungi is Trichoderma. Similarly, CBHI core may be expressed by a host capable of producing a cellulase enzyme mixture (comprising CBHI, CBHII, EG I, EG II, and β-glucosidase).

This invention embraces a cellulase composition comprising a CBHI type enzyme, for example obtained from Trichoderma, and one or more of CBHII, EG I, EG II, and β-glucosidase, wherein CBHI core is present in the cellulase composition at an amount relative to all CBHI-type enzyme of from about 15 to about 100 wt %. Preferably the CBHI core is from about 50 to about 100 wt %, and more preferably from about 80 to about 100 wt %.

Also included in the present invention is a cellulase composition comprising modified CBHI and one or more non-CBHI enzymes, for example but not limited to CBHII, EG I, EG II, and β-glucosidase, wherein the modified CBHI is present in the cellulase composition from about 50 to about 90 wt % relative to other cellulase enzymes as would be known to one of skill in the art. Other cellulase enzymes may include native enzymes in addition the enzymes listed above, for example but not limited to EG III, or derivatives of native cellulase enzymes that exhibit cellulase activity including but not limited to CBHII, EG I, EGII, EG III, or β-glucosidase. Preferably the modified CBHI is a modified Trichoderma CBHI.

Also contemplated by an aspect of an embodiment of the present invention, there is provided a method for converting cellulose to glucose using an enzyme mixture comprising CBHI, and a modified CBHI, for example CBHI core plus linker, and one or more other cellulase enzymes, including CBHII, EG I, EGII, and beta-glucosidase, wherein the weight ratio of CBHI core plus linker in the enzyme mixture is about 50% to about 100 wt % of the CBHI-type enzymes. Preferably, the amount of CBHI core plus linker is about 70% to about 100 wt % of the CBHI-type enzymes. More preferably, the amount of CBHI core plus linker is about 80% to about 100 wt % of the weight of CBHI-type enzymes.

If the modified CBHI includes CBHI with inactivated cellulose binding domain, then enzyme mixtures comprising CBHI with inactivated cellulose binding domain and one or more other cellulase enzymes, including CBHII, EG I, EGII, and beta-glucosidase, comprise a weight ratio of CBHI with inactive cellulose binding domain in the enzyme mixture is about 70% to about 100% of the CBHI-type enzymes. Preferably, the amount of CBHI with inactive binding domain is about 80% to about 100 % of the CBHI-type enzymes.

Further contemplated by an aspect of an embodiment of the present invention, there is provided a method for converting cellulose to glucose using an enzyme mixture comprising CBHI with an inactive cellulose binding domain. Inactivation of the CBHI CBD maybe accomplished using any suitable method as would be known within the art, for example but not limited to the method of Linder et al., (1995, cited above; which is herein incorporated by reference) or Linder et al., (1999, cited above; which is herein incorporated by reference). These references describe changes to single amino acids within the CBD of CBHI that result in partial or complete loss in the capacity for the CBD to bind cellulose. Other methods for inactivation of the CBD may include deletion of a portion of the CBD, or insertion of a peptide sequence within the CBD in order to disrupt CBD binding activity.

Persons skilled in the art are aware that cellulose hydrolysis may occur under a variety of conditions. Preferably, cellulose hydrolysis is performed by cellulase enzymes in a slurry of water and cellulase comprising about 0.5% to about 15% cellulose at a pH of about 4 to about 5 and at a temperature of about 50° C. These conditions are suitable for most cellulase enzymes. However, the present invention also contemplates hydrolyzing cellulose under other conditions which may be better suited to a particular cellulase/CBHI core, CBHI-CBHI core, or other mixtures comprising modified CBHI as defined herein. Such conditions may be readily determined by one of skill in the art.

Any source of cellulase enzyme system may be used in accordance with the method of the present invention. Preferably, cellulase enzymes are from Trichoderma longibrachiatum, and Trichoderma reesei, or a combination thereof. Furthermore, the CBHI and modified CBHI, for example but not limited to CBHI core, proteins are also preferably obtained from *T. longibrachiatum,* and *T reesei,* or a combination thereof.

The crude *Trichoderma* cellulase enzymes used as a basis for in the method of the present invention may be obtained directly through culture of the appropriate microorganism, or the enzymes may be purchased commercially (e. g, from Iogen Corporation). CBHI core may be obtained by expressing the appropriate genetic sequence in a suitable host cell, as is commonly performed in the art, and as described in U.S. Pat. No. 5,874,276 (which is incorporated herein by reference) or CBHI core may be prepared by enzymatic cleavage of CBHI as described above. Similarly, CBHI plus linker may be obtained by expressing a nucleotide sequence comprising the CBHI core and linker region, or via proteolytic cleavage of the holoenzyme. CBHI within inactive cellulose binding domain may be obtained as described above, by expressing the appropriate gene sequence encoding an inactive CBD either through substitution, deletion or insertion, or as would be known by one of skill in the art.

The skilled practitioner will realize that the amount of cellulase enzyme to be used in the hydrolysis of cellulose to glucose may be determined by the nature of the cellulosic substrate, the pretreatment process, the cost of the enzymes, the desired hydrolysis time, and the desired glucose yield from the cellulosic substrate. A typical enzyme dosage range is about 1 to about 50 Filter paper units (FPU) cellulase per gram cellulose for a period of time from about 3 to about 200 hours. In a preferred embodiment the cellulase enzyme dosage is from about 1 to about 10 FPU per gram cellulose.

The skilled practioner is aware that the cellulose concentration is chosen to accommodate the capabilities of pumps to handle and mix the solids. Depending on the material, a cellulose concentration of from about 1% to about 25% is used. However, as described herein, it has been observed that higher cellulose concentrations favour hydrolysis using modified CBHI, for example but not limited to CBHI core (see Example 3). A preferred concentration of cellulose within the reaction mixture is from about 10% to about 16%. A more preferred embodiment is a cellulose concentration of from about 12% to about 16%.

FIG. 1, shows the percentage conversion of cellulose to glucose for a pretreated lignocellulosic substrate, in this case pretreated washed corn stover, using various amounts of CBHI or CBHI core protein. The percent conversion of either pretreated lignocellulosic substrate after a three hour reaction, is greater with CBHI core protein than with the CBHI enzyme at enzyme concentrations between about 1 and about 10 mg enzyme per gram of cellulose. Similar results have also been observed for other pretreated lignocellulosic substrates, including but not limited to, oat hulls, corn stover, and wheat straw (results summarized in FIG. 3).

Figure 2A:
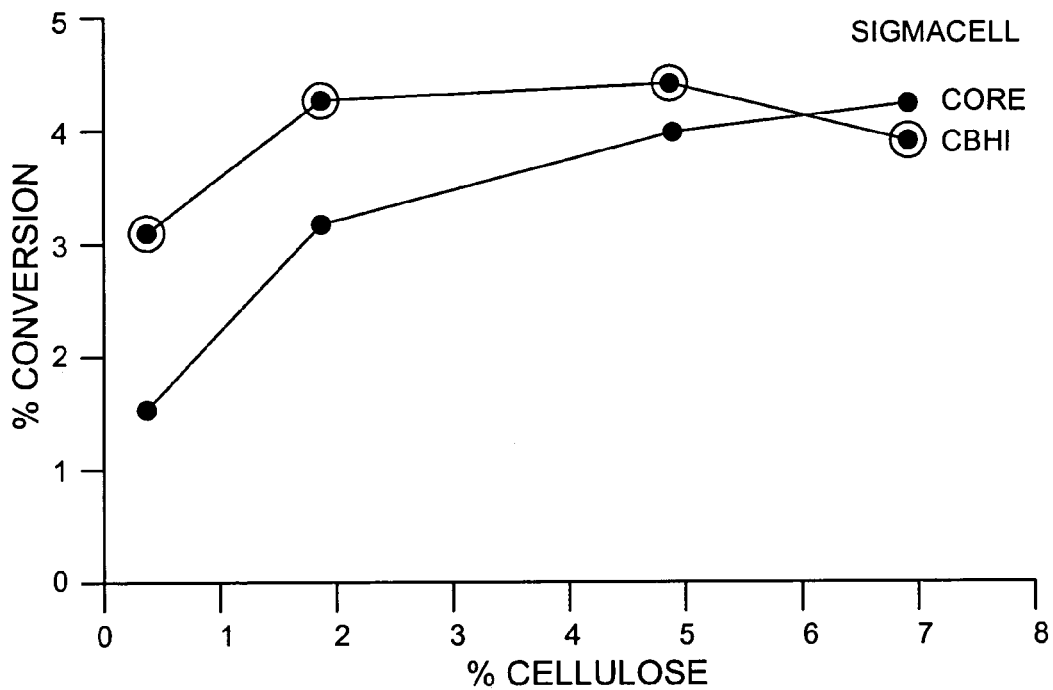
FIG. 2(A) shows the hydrolysis of cellulose to glucose using varying concentrations of SIGMACELL™.

The effect of increasing the concentration of cellulosic substrate in the reaction mixture was also examined, and a sample of the results, using SIGMACELL™ or pretreated hardwood are presented in FIGS. 2(A), (B) and (C). In general, increased conversion from cellulose to glucose by CBHI core was observed, with increased concentration of the cellulosic substrate. As shown in FIG. 2(C), the activity of CBHI typically exceeds that of CBHI core (ratio of CBHI core: CBHI <1) at low concentrations of substrate, however, at higher concentrations of substrate, CBHI core activity exceeds that of CBHI. These data also suggest that increased CBHI core activity (relative to CBHI activity) is observed at different substrate concentrations depending upon the substrate used. However, with all substrates tested, an increase in substrate concentration resulted in an increase in substrate conversion using CBHI core. In the case of SIGMACELL™, CBHI core activity exceeds holoenzyme activity at about 6 to about 7 wt % substrate concentration, while on pretreated hardwood, this threshold is reached at about 3 wt % cellulose. However, it is to be understood that even though core activity exceeds holoenzymne activity at a certain substrate concentration depending upon the substrate, core protein is still active in more dilute cellulose solutions with a pretreated lignocellulosic substrate. Therefore, CBHI core may still be effectively used at lower substrate concentrations, if desired. Consideration of the amount of CBHI core and substrate to be used will depend upon several variables of the reaction mixture including the reaction time, temperature of reaction, cellulosic substrate to be hydrolysed, etc., as would be known to one of skill in the art.

Analysis of the adsorption of either CBHI or CBHI core to different cellulosic substrates (see Table 3, example 1) indicates that for most substrates, CBHI core can be effectively recovered, while CBHI is more readily retained by the substrate. The amount of CBHI core recoverable from a reaction mixture can be expressed as a "Recoverability Index" or "$R_I$", where $R_I$ is a measure of the protein, in this case CBHI+CBHI core, in solution as a function of the total protein, i.e. CBHI+ CBHI core added initially:

$$R_I = [\text{amount of protein in solution}]/[\text{total protein added initially}] \times 100$$

The determination of $R_I$ is made at a constant substrate concentration, for example, as described herein, at 2% cellulose. Using pretreated hardwood (e. g. poplar) as the lignocellulosic substrate, at a 2% cellulose concentration, an $R_I$ of 96 is observed in reactions mixtures comprising 100% CBHI core. This indicates that about 96% of the enzyme added is recoverable from the reaction mixture. In mixtures comprising 50% CBHI core and 50% CBHI, the $R_I$ is about 60, while in mixtures comprising 100% CBHI, the $R_I$ is about 24. These data are consistent with earlier reports that CBHI binds cellulose preferentially and is not easily removed from the substrate.

The results presented in FIGS. 1 to 4 demonstrate that a variety of pretreated cellulosic substrates, preferably lignocellulosic substrates, are well suited for hydrolysis using CBHI core protein. In several instances, and under certain conditions, the absolute rate of hydrolysis is higher using CBHI core when compared to CBHI, even though the amount of CBHI core bound to the substrate at any given time is low, often less than about 10% (see FIG. 3, where $R_I > 90$).

Therefore, this invention is directed to the hydrolysis of cellulosic substrates using a modified CBHI, for example but not limited to a CBHI core protein, that is characterized by having a low tendency to bind to cellulosic substrates, but still exhibits high activity.

The present invention also pertains to a method for the hydrolysis of a cellulosic substrate comprising adding a sufficient amount of modified CBHI, for example but not limited to CBHI core, to a cellulase enzyme mixture and allowing the reaction to proceed for a period of time sufficient to hydrolyze cellulose to glucose.

The present invention provides for a method for the hydrolysis of a cellulosic substrate using mixtures of CBHI and CBHI core proteins, over a range of mixtures from about 20 wt % CBHI core and about 80 wt % CBHI, to about 100 wt % CBHI core.

With reference to FIG. 1A there is shown the percentage conversion of cellulose to glucose from washed corn stover after three hours of incubation with CBHI or CBHI core protein. There is an increase in the conversion of cellulose to glucose with increasing CBHI and CBHI core dosage. At all dosages, CBHI core reaches a higher conversion than CBHI.

Referring now to FIGS. 1B and C there is shown the percentage conversion of cellulose to glucose from pretreated oat hulls and hardwood, respectively, after three hours of incubation in the presence of various combinations of CBHI-CBHI core protein. The greatest conversion of cellulose to glucose is observed for a mixture of CBHI and CBHI core protein comprising about 20 wt % CBHI and about 80 wt % CBHI core protein to about 80 wt % CBHI and about 20 wt % CBHI core.

The results for hydrolysis of cellulose using modified CBHI, for example but not limited to CBHI core, or CBHI and CBHI core protein mixtures, described above, were, unless otherwise indicated, determined in assays comprising 2 % cellulose as a substrate. Results demonstrating the effectiveness of using CBHI core have been also obtained using cellulose concentrations up to about 8 wt %, for agriculture residues, or up to about 12%, for pretreated hardwood (e.g. see FIGS. 2A, B and C). Thus, the present invention contemplates using modified CBHI alone, for example but not limited to CBHI core, or mixtures of CBHI and modified CBHI protein, for example but not limited to CBHI core, to convert cellulose to glucose in mixtures wherein the initial cellulose mixture may comprise from about 0.5 wt % to about 15 wt % by weight cellulose. Preferably, the concentration of cellulose is from about 1 wt % to about 12 wt %. More preferably, the corresponding lignocellulosic substrate, which is about 50% cellulose, is present in the enzyme mixture at a concentration of about 2 wt % to about 25 wt %.

With reference to FIG. 3, there is shown a summary of the activities of CBHI and modified CBHI, in this example, CBHI core, on different lignocellulosic substrates, and the recoverability of these proteins from these substrates. FIG. 3 compares $R_I$ and $E_I$ values for a range of different substrates. Three classes of substrates can be identified from the data presented in FIG. 3:

1) a substrate class characterized as having a low $R_I$ and a low $E_I$ (positioned in the lower lefthand quadrant of the graph; "substrate class one"). An example of such a substrate is Sigmacell™ with an $R_I$ of about 36, and an $E_I$ of about 0.1, demonstrating that the rate of CBHI is much greater than that of CBHI core, and that the recoverability of CBHI core is low;
2) a substrate class characterized as having an intermediate $R_1$, from between about 45 and 75, and an $E_I$ greater than about 0.75 (class positioned in the mid-range of the graph; "substrate class two"). Examples of these substrates include wheat straw with an $R_I$ of about 64, and an $E_I$ of about 1.1, demonstrating that the rate of CBHI core is approximately equivalent to that of CBHI, and that the recoverability of CBHI core is greater than about 50%; and,
3) a third substrate class characterized as having an RI greater than 75; and an $E_I$ greater than 1 ("substrate class three"). Examples of this substrate class include oat hulls (an $R_I$ of about 98, and an $E_I$ of about 0.75), corn straw (an $R_I$ of about 98, and an $E_I$ of about 1.1), H60 (an $R_I$ of about 96, and an $E_I$ of about 1.1), and solka floc (an $R_I$ of about 97, and an $E_1$ of about 3.3).

Figure 4:
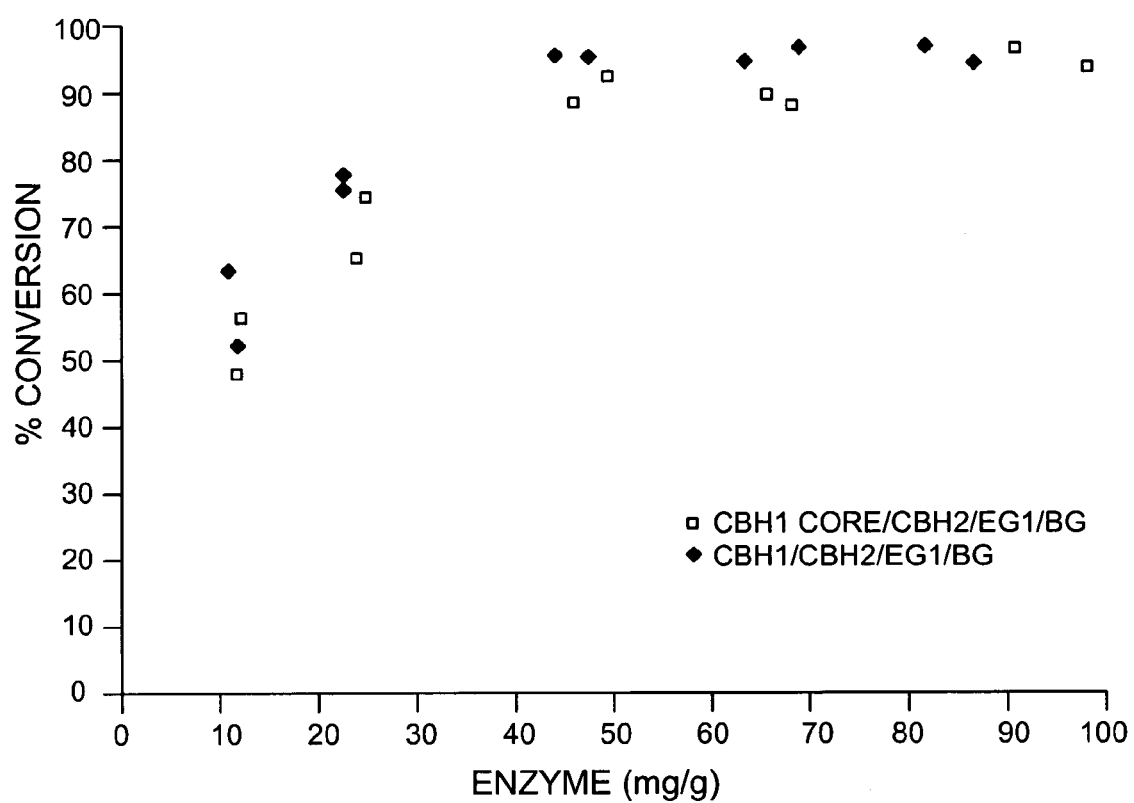
FIG. 4 shows a graphical representation of the relationship of the activity of CBHI and CBHI core in cellulase enzyme mixtures comprising CBH II, EG1 (endoglucanase I) and BG (β-glucosidase).

Referring now to FIG. 4, there is shown results obtained from hydrolysis of pretreated oat hulls by cellulase mixtures comprising CBHI or modified CBHI, for example but not limited to CBHI core. The cellulase mixture comprising modified CBHI exhibits similar results to mixtures comprising CBHI, suggesting that modified CBHI is effective in hydrolysing cellulase mixtures. Further, modified CBHI, for example but not limited to CBHI-core may be more easily recovered than CBHI, and this attribute may be advantageous in cellulose hydrolysis.

Therefore, the present invention is directed to a method for the hydrolysis of a lignocellulosic substrate, using modified CBHI, for example but not limited to CBHI core, or modified CBHI–CBHI mixtures, where the substrate is characterized as being a substrate class two or three substrate. Furthermore, this invention is directed to a method of lignocellulosic hydrolysis wherein the substrate is characterized as having an $E_I$ of at least about 0.75, and an $R_I$ from about 45 to about 100. Preferably, the substrate is characterized as having an $E_I$ of greater than about 1.0, and an $R_I$ of greater than about 60. More preferably, the $E_I$ is from about 1.0 to about 4.0, and the $R_I$ is from about 60 to about 100.

The present invention also pertains to a method for the hydrolysis of a lignocellulosic substrate wherein the substrate is characterized as having an $R_I$ of from about 45 to about 98. Preferably, the $R_I$ is from about 60 to about 98. More preferably, the $R_I$ is from about 80 to about 98.

The present invention also embraces a method for the hydrolysis of a lignocellulosic substrate wherein the substrate is characterized as having an $E_I$ of from about 0.75 to about 4.0. Preferably, the $E_I$ is from about 0.9 to about 4.0. More preferably, the $E_I$ is from about 1 to about 3.6.

The above description is not intended to limit the claimed invention in any manner. Furthermore, the discussed combination of features might not be absolutely necessary for the inventive solution.

The present invention will be further illustrated in the following examples. However, it is to be understood that these examples are for illustrative purposes only, and should not be used to limit the scope of the present invention in any manner.

EXAMPLE 1

Hydrolysis of cellulosic materials by CBHI and CBHI-core and determination of EI The substrates used are listed in Table 1, and enzymes were prepared as follows.

TABLE 1

Cellulose Substrates

| Substrate | Cellulose (%) | Source |
|---|---|---|
| SigmaCell | 100 | Sigma Chemical Co. |
| Solka floe | 92 | Fibre Sales & Dev. Corp. |
| Pretreated wheat straw | 45 | Iogen* |
| Pretreated corn stover | 55 | Iogen* |
| Pretreated poplar | 53 | Iogen* |
| Pretreated oat hulls | 55 | Iogen* |

*as per U.S. Pat. No. 4,461,648; pretreatment process involved adding sulfuric acid from about 0 to about 5%, to a lignocellulosic substrate, and the acidified mixture cooked for about 5 seconds to about 2 minutes, at a temperature of about 180 to about 250° C.

Purified CBHI was obtained from a crude Trichoderma cellulase broth by first filtering the broth through glass microfiber filter paper. The cellulase liquid was then dialyzed using a 10,000 MW cut off membrane in order to lower its conductivity to 12,000 µS. The CBIH was enriched by loading 190 mg protein/mL resin onto pH 6 DEAE Sepharose ion exchange resin. The other components were desorbed from the resin before CBHI, by running 50 mM phosphate, 25 mM NaCl buffer at a conductivity of 9,000 µS through the column.

The CBHI was desorbed by running 50 mM phosphate, 300 mM NaCl buffer at a conductivity of 30,000 µS through the column. The CBHI was then concentrated by ultrafiltration and its purity was accessed by a LKB Bromma isoelectrofucussing electrophoresis unit.

CBHI-core protein was obtained from CBHI by a Quest papain digestion of the pure component at a dosage of 0.05 g papain/g protein for 2 days. The digest pH and temperature were 4.5 and 37° C. respectively. The digest was then filtered through glass microfiber filter paper. The purity of the CBHI is then determined by a LKB Bromma isoelectrofocussing electrophoresis unit.

The hydrolysis mixtures weighed a total of 10 grams. The amount of substrate added was such that 0.2 grams of cellulose was present. In addition, Neodox 23-6 surfactant (4 mg/gram cellulose) was added, along with 80 IU of Novozyme 188 beta-glucosidase, which has a stock activity of 1444 units per milliliter. The surfactant and the beta-glucosidase control foaming and cellobiose formation, respectively. The mixture was brought to a total of 10 grams (excluding CBHI or CBHI-core) with 50 mM sodium citrate buffer, pH 4.8 . The CBHI or CBHI-core dosage was 10 mg protein per gram cellulose.

The mixtures were incubated at 50 C. with shaking at 250 RPM for three hours. At this time, a sample of the mixture was taken and filtered through glass microfiber filter paper. The concentration of glucose in the sample was measured by YSI Glucose Analyzer, of Yellow Springs Instruments, Yellow Springs, Ohio. The glucose concentration is expressed as a percentage conversion of the cellulose in the substrate. The results of incubating the substrates of Table 1 with the above obtained enzymes are listed in Table 2.

TABLE 2

Conversion of cellulose substrates using CBHI or CBHI core protein.

| Substrate | Conversion (%) after 3 hr hydrolysis | | |
|---|---|---|---|
| | CBHI-core | CBHI | Ei |
| SigmaCell | 1.9 | 4.5 | 0.42 |
| Kim et al (1997) | | | 0.14* |
| Van Tilbeurgh et al (1986) | | | 0.01* |
| Nidetsky et al (Filter paper; 1994) | | | 0.44* |
| Corn stover | 14.8 | 13.6 | 1.09 |
| Solka floc | 10.0 | 2.9 | 3.45 |
| Poplar | 6.9 | 7.2 | 0.96 |
| Oat hulls | 7.4 | 9.2 | 0.80 |
| Wheat straw | 9.8 | 9.2 | 1.07 |

*estimated from reported rates of activity of CBHI and CBHI core.

The efficiency index $E_I$ is the ratio of conversion by CBHI-core to CBHI under the conditions used in this example. At $E_I=0$, the CBHI-core is completely unable to hydrolyze the substrate. At $E_I$ between zero and unity, the rate of CBHI-core is lower than the rate of CBHI. At $E_I=1$, the rate of CBHI-core is the same as CBHI. At $E_I>1$, CBHI-core is more rapid than CBHI.

For SigmaCell, the $E_I$ is 0.42 (see FIG. 3). This is consistent with the results of Van Tilbeurgh et al (1986), Kim et al, (1997) and Nidetsky et al (1994), all of whom reported much slower rates of hydrolysis by CBHI-core than by CBHI that correspond to low ratios of CBHI core activity: CBHI activity. This is similar to a low $E_I$, although, the procedures are not the same as those used for $E_I$ determination.

Surprisingly, on the other substrates, $E_I$ is between 0.8 and 1.09, except Solka floc, which was hydrolyzed with an $E_I$ of over 3 (FIG. 3).

The amount of protein in solution was measured for several of the substrates, after three hours of hydrolysis. This measurement was done by a Biorad protein assay using Iogen cellulase (90g/L) as a standard. The results are shown in Table 3.

TABLE 3

Recovery of protein from solution following hydrolysis

| | Protein in solution (%) | |
|---|---|---|
| Substrate | CBHI | CBHI-core |
| Corn stover | 56 | 98 |
| Oat hulls | 51 | 97 |
| Solka floc | 44 | 99 |
| Poplar | 24 | 96 |

The amount of CBHI-core in solution is very high, well over 90% of the total protein. The amount of CBHI in solution is much less. Therefore, CBHI-core offers the opportunity to be recovered and reused, with a rate of hydrolysis virtually as rapid as CBHI.

EXAMPLE 2

Hydrolysis of Pretreated Poplar by Blends of CBHI and CBHI-core

The procedures of Example 1 were repeated, except the CBHI-core and CBHI were used in mixtures. The blends of CBHI/CBHI-core were 0/100, 20/80, 40/60, 60/40, 80/20, and 100/0, as a percent of total protein. The total protein was 10 mg per gram cellulose.

Figure 1C:
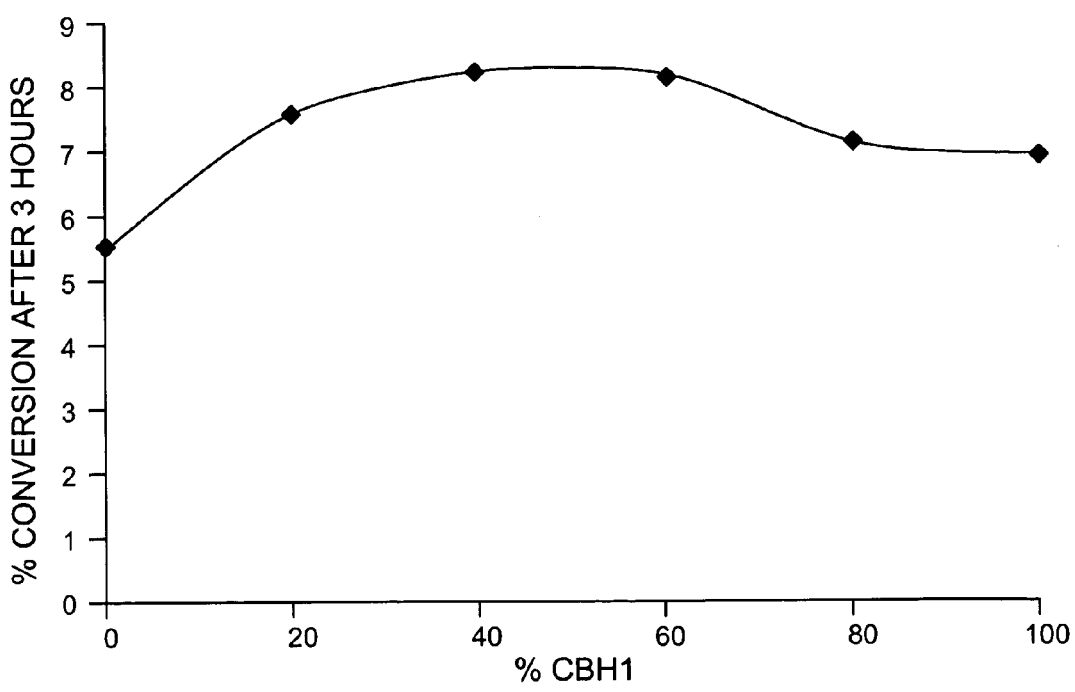
FIG. 1C shows a graphical representation of the percentage conversion of cellulose to glucose from pretreated poplar after three hours of incubation using various combinations of CBHI and CBHI core protein.

The results for pretreated oat hulls as a substrate are shown in FIG. 1B, and for pretreated hardwood (poplar), are presented in FIG. 1C. Surprisingly, the blends of CBHI/CBHI-core of 20/80, 40/60, 60/40, and 80/20 outperform CBHI alone (100/0). This suggests a synergy exists between CBHI and CBHI-core. The optimum mixture, about 50/50, is 20% more efficient than CBHI itself.

EXAMPLE 3

Hydrolysis at Various Cellulose Concentrations

The procedures of Example 1 were repeated, except the cellulose concentration was 0.5%, 2%, 5%, and 10%.

Figure 2B:
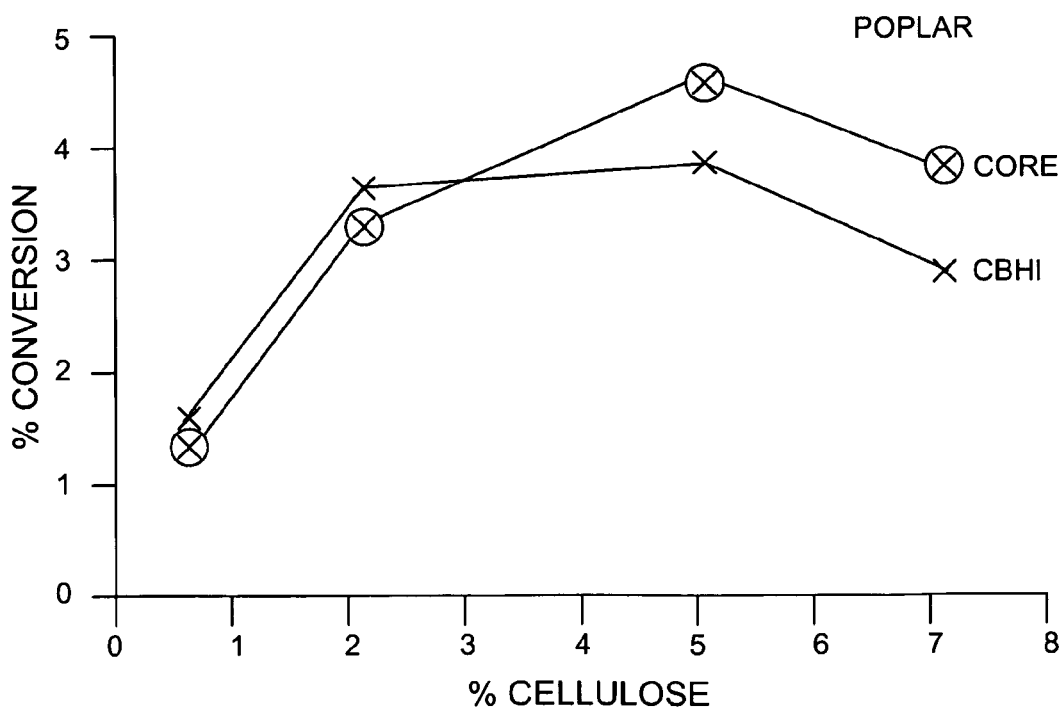
FIG. 2(B) show the hydrolysis of cellulose to glucose using varying concentrations of pretreated poplar.
Figure 2C:
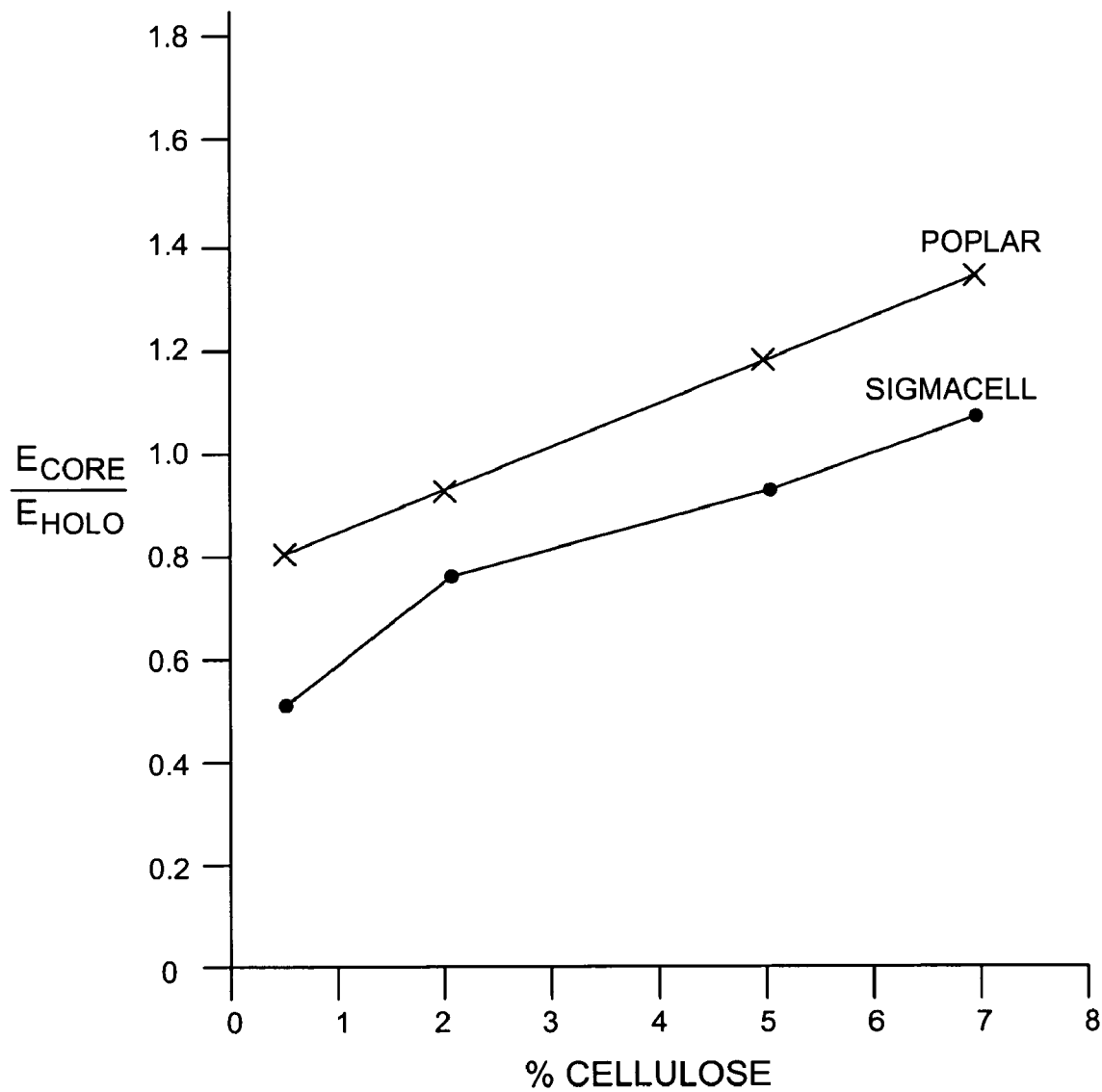
FIG. 2(C) shows a summary of the data obtained from FIGS. 2(A) and 2(B) comparing the $E_f$ with varied concentration of substrate.

The results are shown in FIG. 2. As the cellulose concentration is increased, the $E_I$ values increase on SigmaCell (FIG. 2A), and poplar (FIG. 2B). High cellulose concentration favors CBHI-core in hydrolysis (FIG. 2C).

EXAMPLE 4

Method for Determination of Modified CBHI Proteins as a Percentage of All CBHI-type Enzyme.

A PAGE Beckman MDQ capillary electrophoresis instrument in the capillary isoelectric focusing mode (CIEF) was used to determine the amount of CBHI core, CBHI core plus linker, phosphorylated CBHI, and holoenzyme in a sample of CBHI obtained from Trichoderma. CIEF is a two step process involving 1) focusing, and 2) mobilization. A 10 µL sample of 10% protein is mixed with 200 µL of neutral ampholite and injected in a capillary. A pH gradient (from pH 3-10) is created by the ampholytes under the influence of an electric field. The proteins migrate in the direction opposite their charge until they reach a neutral state where they are focused. This is followed by a low pressure mobilization (at 0.8 psi) of the proteins where they are scanned by a UV detector at 280 nm. An electropherogram is generated showing peaks corresponding to absorbance readings at particular migration times. By using protein standards, different peaks can be identified according to known pI values.

Under these conditions, Trichoderma CBHI exhibits a typical migration time of about 22.1 min, Trichoderma CBHI core plus linker a migration time of about 22.5 minutes, Trichoderma CBHI core a migration time of about 24.7 min, and Trichoderma phosphorylated CBHI of about 23 minutes. These migration times can vary by about ±2 minutes and are routinely checked using standards. The concentration of the proteins is determined from the area of the peaks corresponding to the proteins, for example as indicated in Table 4.

TABLE 4

Composition of Trichoderma CBHI components in prior art Cellulase Enzymes

| Cellulase Iogen Cellulase | Total CBHI-type (%) | % CBHI | % CBHI-core | % CBHI-core plus linker | % phosphorylated CBHI |
|---|---|---|---|---|---|
| 240-226 | 74.5 | 70 | 4.7 | 19.4 | 5.8 |
| 230-812 | 74.5 | 36.7 | 11.9 | 39 | 12.4 |
| 230-799 | 70.3 | 56.7 | 9.4 | 22.9 | 11 |
| 230-685 | 70.8 | 73.1 | 6.3 | 16.3 | 4.4 |
| 230-330 | 72.4 | 65.2 | 7 | 24 | 3.7 |

EXAMPLE 5

Hydrolysis of Pretreated Oat Hulls by Cellulase Mixtures Comprising CBHI Core

Samples of 0.226 grams of steam-pretreated oat hulls (dry basis) are suspended in 50 mM sodium citrate buffer plus 0.5% sodium benzoate, pH 5.0, to a total weight of 2.5 grams in 15 mL centrifuge tubes. The suspension constituted 5% cellulose. To one set of tubes, a mixture of CBHI-core along with CBHII, EGI, and beta-glucosidease is added. The relative amounts of CBHI/CBHII/EGI are 60%/20%/20%, respectively. In addition, Novozym 188 Beta-glucosidase is added at a concentration of 125 BG units per gram cellulose. To a second set of tubes, CBHI-core is replaced with CBHI, with the rest of the mixture unchanged. The total enzyme dosages is between 12 and 95 mg per gram of cellulose, excluding the beta-glucosidase. The flasks are incubated at 50° C., and shaken for 24 hours. At this time, samples are taken and analyzed for residual cellulose concentration. The cellulose concentration is determined by centrifuging the slurry, washing with water, and suspending in 82% sulfuric acid to obtain a net sulfuric acid concentration of 70%. The slurry is incubated at 40° C. for 30 minutes, followed by diluting in deionized water to 2% sulfuric acid. At this time point, the samples are steam-autoclaved at 121° C. for 1 hour, to convert the oligomers to monomeric glucose. The glucose concentration is measured and is compared to the initial cellulose concentration to determine the percentage cellulose conversion.

Results obtained from hydrolysis of pretreated oat hulls by cellulase mixtures comprising CBHI core are shown in FIG. 4. The cellulase mixture comprising CBHI-core exhibits the same results to mixtures comprising CBHI, demonstrating that CBHI-core is effective in hydrolysing cellulose using cellulase mixtures. Further, as CBHI-core, or any other modified CBHI enzyme, may be recovered following cellulose hydrolysis, modified CBHI may be recycled and reused reducing costs associated with glucose production.

All citations are herein incorporated by reference.

The present invention has been described with regard to preferred embodiments. However, it will be obvious to persons skilled in the art that a number of variations and modifications can be made without departing from the scope of the invention as described herein.

REFERENCES

Beldman et al., (1987) Biotechnol. Bioeng. 30, 251-257.
Fan et al., Evaluation Of Pretreatments For Enzymatic Conversion Of Agricultural Residues, Proceedings of the Third Symposium on Biotechnology in Energy Production and Conservation, (Gatlinburg, Tennessee, May 12-15,1981).
Foody, et al, Final Report, Optimization of Steam Explosion Pretreatment, U.S. Department of Energy Report ET230501 (April 1980).
Gilkes et al, (1992) J. Biol. Chem 267, 6743-6749.
Grethlein and Converse (1991) Bioresource Technology 36(2):77-82.
Grohmann, et al, Optimization of Dilute Acid Pretreatment of Biomass, Seventh Symposium on Biotechnology for Fuels and Chemicals (Gatlinburg, Tennessee, May 14-17, 1985).
Kim et al., (1997) Biotechnology Letters. Vol 19 No 9, 893-897.
Knappert, et al., A Partial Acid Hydrolysis of Cellulosic Materials as a Pretreatment for Enzymatic Hydrolysis, Biotechnology and Bioengineering 23:1449-1463 (1980)
Kotiranta et al., (1999) Applied Biochemistry and Biotechnology 81, 81-90.
Kyriacou et al., (1989) Biotechnol. Bioeng. 33, 631-637.
Linder et al (1995) Protein Science 4:1056-1064
Linder et al (1999) FEBS Letters 447:13-16
Neiditsky et al., (1994) Biochem. J. 303, 817-823.
Penttila, M. et al., (1986) Gene 45, 253-263
Saloheimo, M et al., (1988) Gene 63, 11-21
Saloheimo et al., (1993) in Proceedings of the second Tricel symposium of *Trichoderma reesei* Cellulases and other hydrolases, Espoo, Finland, et by P.Suominen and T.Reinikainen. Foundation for Biotechnical and Industrial Fermentation Research 8: 139-146.
Schulein, M. (1988) Methods in Enzymology 160, 235-242.
Shoemaker et al., (1983) Bio/Technology 1, 691-696;
Teeri et al., (1992) J. Biotechnology 24, 169-176.
Teeri et al., (1987) Gene 51, 43-52.
Teeri. T.T. and Koivuval A. (1995) Carbohydr. Eur. 12, 28.
Tomme et al., (1988) Eur. J. Biochem 170, 570-581.
Van Tilbeurgh et al., (1986) FEBS 204, 223-227

The embodiments of the invention in which an exclusive property or privilege is claimed are defined as follows:

1. A method of converting cellulose within a cellulosic substrate to glucose, comprising:
   (a) treating a lignocellulosic substrate with a purified enzyme mixture, said purified enzyme mixture comprising:
   (i) cellobiohydrolase I (CBHI) enzyme, wherein said CBHI enzyme is a CBHI core or unmodified CBHI, wherein the CBHI core is present in an amount from 55 to 100% by weight relative to all CBHI enzyme in the enzyme mixture; and (ii) cellulase enzymes, wherein said cellulase enzymes comprise an endoglucanase (EG), an exo-cellobiohydrolase (CBH), and β-glucosidase, thereby providing glucose in an amount greater than an amount provided by the use of unmodified CBHI alone; and, (b) recovering said glucose.

2. The method of claim 1 wherein said amount of CBHI core in said enzyme mixture is from 70 to 100% by weight relative to all CBHI enzyme.

3. The method of claim 1 wherein said amount of CBHI core in said enzyme mixture is from 80 to 100% by weight relative to all CBHI enzyme.

4. A method of converting cellulose within a cellulosic substrate into glucose, comprising:
(a) treating a lignocellulosic substrate with a purified enzyme mixture, said purified enzyme mixture comprising:
  (i) cellobiohydrolase I (CBHI) enzyme, wherein said CBHI enzyme is a CBHI core or unmodified CBHI, wherein the CBHI core is present in an amount from 55 to 100% by weight relative to all CBHI enzyme in the enzyme mixture; and
  (ii) cellulase enzymes, wherein said cellulase enzymes comprise endoglucanase I (EGI), endoglucanase II (EGII), cellobiohydrolase II (CBHII), and β-glucosidase,
thereby providing glucose in an amount greater than an amount provided by the use of unmodified CBHI alone; and,
(b) recovering said glucose.

5. The method of claim 4, wherein said amount of CBHI core in said enzyme mixture is from 70 to 100% by weight relative to all CBHI enzyme.

6. The method of claim 5, wherein said amount of CBHI core in said enzyme mixture is from 80 to 100% by weight relative to all CBHI enzyme.

7. The method of claim 1, further comprising (c) recovering said CBHI core following said treating of step (a).

8. The method of claim 7, further comprising (d) reusing said CBHI core recovered in step (c).

9. The method of claim 4, further comprising (c) recovering said modified CBHI following said treating of step (a).

10. The method of claim 9, further comprising (d) reusing said CBHI core recovered in step (c).

11. The method of claim 1, wherein said lignocellulosic substrate is selected from the group consisting of agricultural residues, residues after starch or sugar removal, dedicated ethanol crops, forestry products, and pulp and paper products, or combinations thereof.

12. The method of claim 11 wherein:
said agricultural residues are selected from the group consisting of corn stover, wheat straw, barley straw, and soybean stover;
said residues after starch or sugar removal are selected from the group consisting of oat hulls, rice hulls, sugar case bagasse, and corn fibre;
said dedicated ethanol crops are selected from the group consisting of switch grass, *Miscanthus*, cord grass, and rye grass; and
said forestry products are selected from the group consisting of hardwood, softwood, *Eucalyptus*, and sawdust.

13. A method of converting cellulose within a cellulosic substrate to glucose, comprising:
(a) treating a lignocellulosic substrate with a purified enzyme mixture, said purified enzyme mixture comprising:
  (i) cellobiohydrolase I (CBHI) enzyme, wherein said CBHI enzyme is a CBHI core or unmodified CBHI, wherein the CBHI core is present in an amount from 55 to 100% by weight relative to all CBHI enzyme in the enzyme mixture; and
  (ii) cellulase enzymes, wherein said cellulase enzymes comprise an endoglucanase (EG), an exo-cellobiohydrolase (CBH), and β-glucosidase, for a period of time sufficient to hydrolyze said cellulose, thereby providing glucose in an amount greater than an amount provided by the use of unmodified CBHI alone;
(b) recovering said glucose; and,
(c) recovering said modified CBHI from said enzyme mixture.

14. The method of claim 1, wherein said lignocellulosic substrate is characterized as having a CBHI core:CBHI efficiency index ($E_I$) of at least 0.5.

15. The method of claim 14, wherein said $E_I$ is from 0.5 to 4.0.

16. The method of claim 14, wherein said $E_I$ is from 1.0 to 4.0.

17. The method of claim 15, wherein said $E_I$ is from 0.7 to 2.0.

18. The method of claim 15, wherein said $E_I$ is from 0.8 to 1.5.

19. The method of claim 1, wherein in said treating step (a) the amount of cellulose present in said substrate is from 0.5 to 15% by weight relative to the weight of the enzyme mixture.

20. The method of claim 19 wherein in said treating step (a) the amount of cellulose present in said substrate is from 1 to 12% by weight relative to the weight of the enzyme mixture.

21. A method of hydrolyzing cellulose within a cellulosic substrate to glucose, comprising:
(a) treating a lignocellulosic substrate with a purified enzyme mixture, the enzyme mixture comprising:
  (i) cellobiohydrolase I (CBHI) enzyme, wherein said CBHI enzyme is a CBHI core or unmodified CBHI and wherein said CBHI enzyme comprises 20 to 100% by weight CBHI core, and
  (ii) cellulase enzyme, wherein said lignocellulosic substrate is characterized by having a CBHI core: unmodified CBHI efficiency index (Li) of from 0.5 to 4 and, thereby providing glucose in an amount greater than an amount provided by the use of unmodified CBHI alone; and,
(b) recovering said glucose.

22. The method of claim 21, wherein said recovering in step (b) comprises recovering using an ultrafiltration membrane.

23. The method of claim 21, wherein the substrate contains cellulose in an amount from 1 to 12% by weight relative to the weight of said substrate.

24. The method of claim 21, wherein said lignocellulosic substrate is selected from the group consisting of agricultural residues, residues after starch or sugar removal, dedicated ethanol crops, forestry products, and pulp and paper products, or combinations thereof.

25. The method of claim 24 wherein:
said agricultural residues are selected from the group consisting of corn stover, wheat straw, barley straw, soybean stover;
said residues after starch or sugar removal are selected from the group consisting of oat hulls, rice hulls, sugar cane bagasse, and corn fibre;

said dedicated ethanol crops are selected from the group consisting of switch grass, *Miscanthus*, cord grass, and rye grass; and said forestry products are selected from the group consisting of hardwood, softwood, *Eucalyptus*, and sawdust.

26. The method of claim 1, wherein said lignocellulosic substrate is pretreated using an acid steam cook prior to said treatment with said purified enzyme mixture.

27. A method of converting cellulose within a cellulosic substrate into glucose, comprising:

(a) treating a lignocellulosic substrate, with a purified enzyme mixture, said enzyme mixture comprising: cellobiohydrolase I (CBHI), cellobiohydrolase II (CBHII), endoglucanase I (EGI), endoglucanase II (EGII), and β-glucosidase, wherein said CBHI enzyme is a CBHI core or unmodified CBHI, wherein the CBHI core is present in an amount from 55 to 100% by weight relative to all CBHI enzyme, thereby providing glucose in an amount greater than an amount provided by the use of unmodified CBHI alone; and, (b) recovering said glucose.

28. The method of claim 27, wherein said CBHI core is present in said enzyme mixture from 50 to 100% by weight relative to all CBHI enzymes.

29. The method of claim 27, wherein said CBHI core is present in said enzyme mixture from 80 to 100% by weight relative to all CBHI enzymes.

30. The method of claim 1 wherein said CBHI core is obtained from *Trichoderma* CBHI.

31. The method of claim 4, wherein said CBHI core is obtained from *Trichoderma* CBHI.

32. The method of claim 13, wherein said CBHI core is obtained from *Trichoderma* CBHI.

33. The method of claim 21, wherein said CBHI core is obtained from *Trichoderma* CBHI.

34. The method of claim 27 wherein said CBHI core is obtained from *Trichoderma* CBHI.

35. The method of any one of claims 1-3,4,5,7-13,14-21, 22-25,27-29 or 30-34, wherein the lignocellulosic substrate comprises at least 10% lignin by weight.

36. The method of any one of claims 1-3,4,5,7-13,14-21, 22-25,27-29 or 30-34, wherein said lignocellulosic substrate of step (a) is an acid steam cooked lignocellulosic substrate.

* * * * *

UNITED STATES PATENT AND TRADEMARK OFFICE
CERTIFICATE OF CORRECTION

PATENT NO. : 7,419,809 B2
APPLICATION NO. : 10/381442
DATED : September 2, 2008
INVENTOR(S) : Brian Foody et al.

Page 1 of 3

It is certified that error appears in the above-identified patent and that said Letters Patent is hereby corrected as shown below:

ON TITLE PAGE AT (*) NOTICE

Insert: --This patent is subject to a terminal disclaimer--.

ON TITLE PAGE AT (56) OTHER PUBLICATIONS

After "Chen, et al.,": "Cellobiohyrdolase" should read --Cellobiohydrolase--; and
    After "Tomme, et al., . . . (1988) 575-81.": "Suurnakki, et al., *Trichoderma reesei* Cellulases and their Core Domains in the Hydriolysis and Modification of Chemical Pulp"; Cellulose, vol. 7 (2000) 189-209." should be deleted.

COLUMN 1

Line 35, "CBBE" should read --CBHII--; and
    Line 63, "Polo)" should read --(holo)--.

COLUMN 2

Line 6, "substrates" should read --substrate--.

COLUMN 3

Line 61, "CBI-H1," should read --CBHII,--; and "β" should read --β- --.

COLUMN 4

Line 5, "CBHJ" should read --CBHI--.

COLUMN 7

Line 17, "hulls" should read --hulls,--.

COLUMN 9

Line 25, "maybe" should read --may be--; and
    Line 57, "manner" should read --manner,--.

UNITED STATES PATENT AND TRADEMARK OFFICE
CERTIFICATE OF CORRECTION

| | |
|---|---|
| PATENT NO. | : 7,419,809 B2 |
| APPLICATION NO. | : 10/381442 |
| DATED | : September 2, 2008 |
| INVENTOR(S) | : Brian Foody et al. |

It is certified that error appears in the above-identified patent and that said Letters Patent is hereby corrected as shown below:

COLUMN 11

Line 56, "fungi." should read --fungus.--; and
    Line 57, "fungi" should read --fungus--.

COLUMN 12

Line 31, "is" should read --that is--.

COLUMN 14

Line 32, "reactions" should read --reaction--.

COLUMN 16

Line 63, "CBIH" should read --CBHI--.

COLUMN 17

Line 4, "isoelectrofu-" should read --isoelectrofo- --; and
    Line 25, "50 C." should read --50 °C.--.

COLUMN 18

Line 2, "Solka" should read --solka--; and
    Line 67, "ampholite" should read --ampholyte--.

COLUMN 19

Line 50, "is" should read --are--.

COLUMN 20

Line 40, "After "Linder et al (1999)": "Neiditsky" should read --Nidetzky--.

COLUMN 21

Line 57, "case" should read --cane--.

UNITED STATES PATENT AND TRADEMARK OFFICE
CERTIFICATE OF CORRECTION

PATENT NO. : 7,419,809 B2
APPLICATION NO. : 10/381442
DATED : September 2, 2008
INVENTOR(S) : Brian Foody et al.

It is certified that error appears in the above-identified patent and that said Letters Patent is hereby corrected as shown below:

<u>COLUMN 22</u>

Line 44, "(Li)" should read --($E_I$)--; and
Line 45, "4 and," should read --4, and--.

<u>COLUMN 24</u>

Line 7, "claim 1" should read --claim 1,--;
Line 17, "claims 1-3, 4, 5, 7-13, 14-21," should read --claims 1-5, 7-25 or 27-34,--;
Line 18, "22-25, 27-29 or 30-34," should be deleted;
Line 20, "claims 1-3, 4, 5, 7-13, 14-21," should read --1-5, 7-25, or 27-34,--; and
Line 21, "22-25, 27-29 or 30-34," should be deleted.

Signed and Sealed this

Third Day of March, 2009

JOHN DOLL
*Acting Director of the United States Patent and Trademark Office*